United States Patent
Yang et al.

(10) Patent No.: US 10,294,256 B2
(45) Date of Patent: May 21, 2019

(54) PHOSPHINE OXIDE ALKYL AMIDE SUBSTITUTED HETEROARYL COMPOUNDS AS MODULATORS OF IL-12, IL-23 AND/OR IFN ALPHA RESPONSES

(71) Applicant: BRISTOL-MYERS SQUIBB COMPANY, Princeton, NJ (US)

(72) Inventors: Michael G. Yang, Narbeth, PA (US); Zili Xiao, East Windsor, NJ (US); John V. Duncia, Newtown, PA (US); David S. Weinstein, La Jolla, CA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 15/838,434

(22) Filed: Dec. 12, 2017

(65) Prior Publication Data
US 2018/0162889 A1 Jun. 14, 2018

Related U.S. Application Data

(60) Provisional application No. 62/433,470, filed on Dec. 13, 2016.

(51) Int. Cl.
| | | |
|---|---|---|
| *C07D 401/00* | (2006.01) | |
| *C07F 9/6558* | (2006.01) | |
| *A61P 29/00* | (2006.01) | |
| *A61P 37/00* | (2006.01) | |
| *C07F 9/6509* | (2006.01) | |
| *A61K 31/50* | (2006.01) | |
| *A61K 31/501* | (2006.01) | |
| *C07D 401/12* | (2006.01) | |
| *C07D 237/24* | (2006.01) | |

(52) U.S. Cl.
CPC .......... *C07F 9/65583* (2013.01); *A61K 31/50* (2013.01); *A61K 31/501* (2013.01); *A61P 29/00* (2018.01); *A61P 37/00* (2018.01); *C07D 237/24* (2013.01); *C07D 401/12* (2013.01); *C07F 9/650905* (2013.01)

(58) Field of Classification Search
CPC ........... C07F 9/65583; C07F 9/650905; A61K 31/50; A61K 31/501; C07D 237/34; C07D 401/12; A61P 37/00; A61P 29/00

USPC .......................................................... 544/238
See application file for complete search history.

(56) References Cited

FOREIGN PATENT DOCUMENTS

| WO | WO 2009/143389 A1 | 11/2009 |
| WO | WO 2010/141406 A2 | 12/2010 |
| WO | WO 2013/169401 A1 | 11/2013 |
| WO | WO 2014/074661 A1 | 5/2014 |

OTHER PUBLICATIONS

U.S. Appl. No. 14/441,183, filed May 7, 2015, Granted U.S. Pat. No. 9,505,748.
U.S. Appl. No. 15/289,437, filed Oct. 10, 2016, Allowed.
PCT/US2013/068846, Filing Date: Nov. 7, 2013, Published WO 2014/074661.
U.S. Appl. No. 15/034,915, filed May 6, 2016, Granted U.S. Pat. No. 9,663,467.
U.S. Appl. No. 15/480,787, filed Apr. 6, 2017, Allowed.
PCT/US2014/011769, Filing Date: Jan. 16, 2014, Published WO 2015/069310.
U.S. Appl. No. 62/589,165, filed Nov. 21, 2017, Filed.

*Primary Examiner* — Taylor V Oh
(74) *Attorney, Agent, or Firm* — Elliott Korsen

(57) ABSTRACT

Compounds having the following formula I:

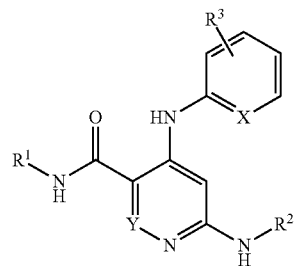

or a stereoisomer or pharmaceutically-acceptable salt thereof, where all substituents are as defined herein, are useful in the modulation of IL-12, IL-23 and/or IFNα, by acting on Tyk-2 to cause signal transduction inhibition.

10 Claims, No Drawings

Specification includes a Sequence Listing.

PHOSPHINE OXIDE ALKYL AMIDE SUBSTITUTED HETEROARYL COMPOUNDS AS MODULATORS OF IL-12, IL-23 AND/OR IFN ALPHA RESPONSES

CROSS-REFERENCE TO RELATED APPLICATIONS

This application claims the benefit of U.S. Provisional Application No. 62/433,470 filed Dec. 13, 2016, the disclosure of which is incorporated herein by reference in its entirety.

FIELD OF THE INVENTION

This invention relates to compounds useful in the modulation of IL-12, IL-23 and/or IFNα by acting on Tyk-2 to cause signal transduction inhibition. Provided herein are compounds, compositions comprising such compounds, and methods of their use. The invention further pertains to pharmaceutical compositions containing at least one compound according to the invention that are useful for the treatment of conditions related to the modulation of IL-12, IL-23 and/or IFNα in a mammal.

BACKGROUND OF THE INVENTION

The heterodimeric cytokines interleukin IL-12 and IL-23, which share a common p40 subunit, are produced by activated antigen-presenting cells and are critical in the differentiation and proliferation of Th1 and Th17 cells, two effector T cell lineages which play key roles in autoimmunity. IL-23 is composed of the p40 subunit along with a unique p19 subunit. IL-23, acting through a heterodimeric receptor composed of IL-23R and IL-12Rβ1, is essential for the survival and expansion of Th17 cells which produce pro-inflammatory cytokines such as IL-17A, IL-17F, IL-6 and TNF-α (McGeachy, M. J. et al., "The link between IL-23 and Th17 cell-mediated immune pathologies", Semin. Immunol., 19:372-376 (2007)). These cytokines are critical in mediating the pathobiology of a number of autoimmune diseases, including rheumatoid arthritis, multiple sclerosis, inflammatory bowel disease, and lupus. IL-12, in addition to the p40 subunit in common with IL-23, contains a p35 subunit and acts through a heterodimeric receptor composed of IL-12Rβ1 and IL-12Rβ2. IL-12 is essential for Th1 cell development and secretion of IFNγ, a cytokine which plays a critical role in immunity by stimulating MHC expression, class switching of B cells to IgG subclasses, and the activation of macrophages (Gracie, J. A. et al., "Interleukin-12 induces interferon-gamma-dependent switching of IgG alloantibody subclass", Eur. J. Immunol., 26:1217-1221 (1996); Schroder, K. et al., "Interferon-gamma: an overview of signals, mechanisms and functions", J. Leukoc. Biol., 75(2):163-189 (2004)).

The importance of the p40-containing cytokines in autoimmunity is demonstrated by the discovery that mice deficient in either p40, p19, or IL-23R are protected from disease in models of multiple sclerosis, rheumatoid arthritis, inflammatory bowel disease, lupus and psoriasis, among others (Kyttaris, V. C. et al., "Cutting edge: IL-23 receptor deficiency prevents the development of lupus nephritis in C57BL/6-lpr/lpr mice", J. Immunol., 184:4605-4609 (2010); Hong, K. et al., "IL-12, independently of IFN-gamma, plays a crucial role in the pathogenesis of a murine psoriasis like skin disorder", J. Immunol., 162:7480-7491 (1999); Hue, S. et al., "Interleukin-23 drives innate and T cell-mediated intestinal inflammation", J. Exp. Med., 203:2473-2483 (2006); Cua, D. J. et al., "Interleukin-23 rather than interleukin-12 is the critical cytokine for autoimmune inflammation of the brain", Nature, 421:744-748 (2003); Murphy, C. A. et al., "Divergent pro- and anti-inflammatory roles for IL-23 and IL-12 in joint autoimmune inflammation", J. Exp. Med., 198:1951-1957 (2003)).

In human disease, high expression of p40 and p19 has been measured in psoriatic lesions, and Th17 cells have been identified in active lesions in the brain from MS patients and in the gut mucosa of patients with active Crohn's disease (Lee, E. et al., "Increased expression of interleukin 23 p19 and p40 in lesional skin of patients with psoriasis vulgaris", J. Exp. Med., 199:125-130 (2004); Tzartos, J. S. et al., "Interleukin-17 production in central nervous system infiltrating T cells and glial cells is associated with active disease in multiple sclerosis", Am. J. Pathol., 172:146-155 (2008)). The mRNA levels of p19, p40, and p35 in active SLE patients were also shown to be significantly higher compared with those in inactive SLE patients (Huang, X. et al., "Dysregulated expression of interleukin-23 and interleukin-12 subunits in systemic lupus erythematosus patients", Mod. Rheumatol., 17:220-223 (2007)), and T cells from lupus patients have a predominant Th1 phenotype (Tucci, M. et al., "Overexpression of interleukin-12 and T helper 1 predominance in lupus nephritis", Clin. Exp. Immunol., 154:247-254 (2008)).

Moreover, genome-wide association studies have identified a number of loci associated with chronic inflammatory and autoimmune diseases that encode factors that function in the IL-23 and IL-12 pathways. These genes include IL23A, IL12A, IL12B, IL12RB1, IL12RB2, IL23R, JAK2, TYK2, STAT3, and STAT4 (Lees, C. W. et al., "New IBD genetics: common pathways with other diseases", Gut, 60:1739-1753 (2011); Tao, J. H. et al., "Meta-analysis of TYK2 gene polymorphisms association with susceptibility to autoimmune and inflammatory diseases", Mol. Biol. Rep., 38:4663-4672 (2011); Cho, J. H. et al., "Recent insights into the genetics of inflammatory bowel disease", Gastroenterology, 140:1704-1712 (2011)).

Indeed, anti-p40 treatment, which inhibits both IL-12 and IL-23, as well as IL-23-specific anti-p19 therapies have been shown to be efficacious in the treatment of autoimmunity in diseases including psoriasis, Crohn's Disease and psoriatic arthritis (Leonardi, C. L. et al., "PHOENIX 1 study investigators. Efficacy and safety of ustekinumab, a human interleukin-12/23 monoclonal antibody, in patients with psoriasis: 76-week results from a randomized, double-blind, placebo-controlled trial (PHOENIX 1)", Lancet, 371:1665-1674 (2008); Sandbom, W. J. et al., "Ustekinumab Crohn's Disease Study Group. A randomized trial of Ustekinumab, a human interleukin-12/23 monoclonal antibody, in patients with moderate-to-severe Crohn's disease", Gastroenterology, 135:1130-1141 (2008); Gottlieb, A. et al., "Ustekinumab, a human interleukin 12/23 monoclonal antibody, for psoriatic arthritis: randomized, double-blind, placebo-controlled, crossover trial", Lancet, 373:633-640 (2009)). Therefore, agents which inhibit the action of IL-12 and IL-23 may be expected to have therapeutic benefit in human autoimmune disorders.

The Type I group of interferons (IFNs), which include the IFNα members as well as IFNβ, IFNε, IFNκ and IFNω, act through a heterodimer IFNα/β receptor (IFNAR). Type I IFNs have multiple effects in both the innate and adaptive immune systems including activation of both the cellular and humoral immune responses as well as enhancing the expression and release of autoantigens (Hall, J. C. et al., "Type I interferons: crucial participants in disease amplification in autoimmunity", *Nat. Rev. Rheumatol.*, 6:40-49 (2010)).

In patients with systemic lupus erythematosus (SLE), a potentially fatal autoimmune disease, increased serum levels of interferon (IFN)α (a type I interferon) or increased expression of type I IFN-regulated genes (a so-called IFNα signature) in peripheral blood mononuclear cells and in affected organs has been demonstrated in a majority of patients (Bennett, L. et al., "Interferon and granulopoiesis signatures in systemic lupus erythematosus blood", *J. Exp. Med.*, 197:711-723 (2003); Peterson, K. S. et al., "Characterization of heterogeneity in the molecular pathogenesis of lupus nephritis from transcriptional profiles of laser-captured glomeruli", *J. Clin. Invest.*, 113:1722-1733 (2004)), and several studies have shown that serum IFNα levels correlate with both disease activity and severity (Bengtsson, A. A. et al., "Activation of type I interferon system in systemic lupus erythematosus correlates with disease activity but not with antiretroviral antibodies", *Lupus*, 9:664-671 (2000)). A direct role for IFNα in the pathobiology of lupus is evidenced by the observation that the administration of IFNα to patients with malignant or viral diseases can induce a lupus-like syndrome. Moreover, the deletion of the IFNAR in lupus-prone mice provides high protection from autoimmunity, disease severity and mortality (Santiago-Raber, M. L. et al., "Type-I interferon receptor deficiency reduces lupus-like disease in NZB mice", *J. Exp. Med.*, 197:777-788 (2003)), and genome-wide association studies have identified loci associated with lupus that encode factors that function in the type I interferon pathway, including IRF5, IKBKE, TYK2, and STAT4 (Deng, Y. et al., "Genetic susceptibility to systemic lupus erythematosus in the genomic era", *Nat. Rev. Rheumatol.*, 6:683-692 (2010); Sandling, J. K. et al., "A candidate gene study of the type I interferon pathway implicates IKBKE and IL8 as risk loci for SLE", *Eur. J. Hum. Genet.*, 19:479-484 (2011)). In addition to lupus, there is evidence that aberrant activation of type I interferon-mediated pathways are important in the pathobiology of other autoimmune diseases such as Sjögren's syndrome and scleroderma (Båve, U. et al., "Activation of the type I interferon system in primary Sjögren's syndrome: a possible etiopathogenic mechanism", *Arthritis Rheum.*, 52:1185-1195 (2005); Kim, D. et al., "Induction of interferon-alpha by scleroderma sera containing autoantibodies to topoisomerase I: association of higher interferon-alpha activity with lung fibrosis", *Arthritis Rheum.*, 58:2163-2173 (2008)). Therefore, agents which inhibit the action of type I interferon responses may be expected to have therapeutic benefit in human autoimmune disorders.

Tyrosine kinase 2 (Tyk2) is a member of the Janus kinase (JAK) family of nonreceptor tyrosine kinases and has been shown to be critical in regulating the signal transduction cascade downstream of receptors for IL-12, IL-23 and type I interferons in both mice (Ishizaki, M. et al., "Involvement of Tyrosine Kinase-2 in Both the IL-12/Th1 and IL-23/Th17 Axes In vivo", *J. Immunol.*, 187:181-189 (2011); Prchal-Murphy, M. et al., "TYK2 kinase activity is required for functional type I interferon responses in vivo", *PLoS One*, 7:e39141 (2012)) and humans (Minegishi, Y. et al., "Human tyrosine kinase 2 deficiency reveals its requisite roles in multiple cytokine signals involved in innate and acquired immunity", *Immunity*, 25:745-755 (2006)). Tyk2 mediates the receptor-induced phosphorylation of members of the STAT family of transcription factors, an essential signal that leads to the dimerization of STAT proteins and the transcription of STAT-dependent pro-inflammatory genes. Tyk2-deficient mice are resistant to experimental models of colitis, psoriasis and multiple sclerosis, demonstrating the importance of Tyk2-mediated signaling in autoimmunity and related disorders (Ishizaki, M. et al., "Involvement of Tyrosine Kinase-2 in Both the IL-12/Th1 and IL-23/Th17 Axes In vivo", *J. Immunol.*, 187:181-189 (2011); Oyamada, A. et al., "Tyrosine kinase 2 plays critical roles in the pathogenic CD4 T cell responses for the development of experimental autoimmune encephalomyelitis", *J. Immunol.*, 183:7539-7546 (2009)).

In humans, individuals expressing an inactive variant of Tyk2 are protected from multiple sclerosis and possibly other autoimmune disorders (Couturier, N. et al., "Tyrosine kinase 2 variant influences T lymphocyte polarization and multiple sclerosis susceptibility", *Brain*, 134:693-703 (2011)). Genome-wide association studies have shown other variants of Tyk2 to be associated with autoimmune disorders such as Crohn's Disease, psoriasis, systemic lupus erythematosus, and rheumatoid arthritis, further demonstrating the importance of Tyk2 in autoimmunity (Ellinghaus, D. et al., "Combined Analysis of Genome-wide Association Studies for Crohn Disease and Psoriasis Identifies Seven Shared Susceptibility Loci", *Am. J. Hum. Genet.*, 90:636-647 (2012); Graham, D. et al., "Association of polymorphisms across the tyrosine kinase gene, TYK2 in UK SLE families", *Rheumatology (Oxford)*, 46:927-930 (2007); Eyre, S. et al., "High-density genetic mapping identifies new susceptibility loci for rheumatoid arthritis", *Nat. Genet.*, 44:1336-1340 (2012)).

In view of the conditions that may benefit by treatment involving the modulation of cytokines and/or interferons, new compounds capable of modulating cytokines and/or interferons, such as IL-12, IL-23 and/or IFNα, and methods of using these compounds may provide substantial therapeutic benefits to a wide variety of patients in need thereof.

SUMMARY OF THE INVENTION

The invention is directed to compounds of Formula I which are useful as modulators of IL-12, IL-23 and/or IFNα by inhibiting Tyk2-mediated signal transduction.

The present invention also provides processes and intermediates for making the compounds of the present invention.

The present invention also provides pharmaceutical compositions comprising a pharmaceutically acceptable carrier and at least one of the compounds of the present invention.

The present invention also provides a method for the modulation of IL-12, IL-23 and/or IFNα by inhibiting Tyk-2-mediated signal transduction comprising administering to a host in need of such treatment a therapeutically effective amount of at least one of the compounds of the present invention.

The present invention also provides a method for treating proliferative, metabolic, allergic, autoimmune and inflammatory diseases, comprising administering to a host in need of such treatment a therapeutically effective amount of at least one of the compounds of the present invention.

One embodiment is a method for treating inflammatory and autoimmune diseases or diseases. For the purposes of this invention, an inflammatory and autoimmune disease or disorder includes any disease having an inflammatory or autoimmune component.

Another embodiment is a method for treating metabolic diseases, including type 2 diabetes and atherosclerosis.

The present invention also provides the use of the compounds of the present invention for the manufacture of a medicament for the treatment of cancers.

The present invention also provides the compounds of the present invention for use in therapy.

DETAILED DESCRIPTION OF THE INVENTION

In a first aspect of the present invention, there is provided a compound of formula

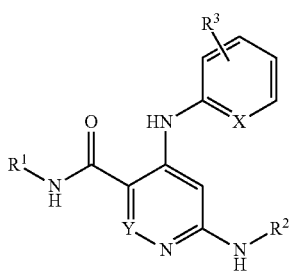

I wherein:
X is —N— or —CH—;
Y is —N— or —CH—;
$R^1$ is $CD_3$, $C_{1-3}$ alkyl or $C_{3-6}$ cycloalkyl;
$R^2$ is CO—$C_{3-6}$ cycloalkyl, $C_{5-8}$ aryl or a 5-7 membered heterocyclyl containing 1-4 heteroatoms selected from N, O, and S, substituted with 0-4 $R^{2a}$;
$R^{2a}$ is independently, at each occurrence, hydrogen, halogen, $C_{1-6}$ alkyl, $C_{1-6}$ alkoxy, $C_{3-6}$ cycloalkyl, halo $C_{1-6}$ alkyl, hydroxy $C_{1-6}$ alkyl, $C_{5-8}$ aryl or a 5-7 membered heterocyclyl containing 1-4 heteroatoms selected from N, O, and S, said aryl or heterocyclyl substituted with 0-2 $R^a$;
$R^a$ is hydrogen, halogen or $C_{1-4}$ alkyl;
$R^3$ is P(O)—$(C_{1-4}$ alkyl$)_2$;
or a stereoisomer or pharmaceutically-acceptable salt thereof.

In a second aspect of the invention, there are provided compounds of formula II,

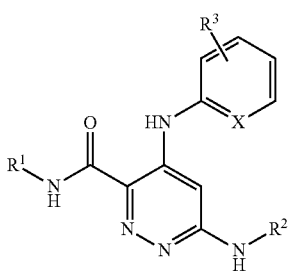

(II)

wherein:
X is —N— or —CH—;
$R^1$ is $CD_3$, $C_{1-3}$ alkyl or $C_{3-6}$ cycloalkyl;
$R^2$ is CO—$C_{3-6}$ cycloalkyl, $C_{5-8}$ aryl or a 5-7 membered heterocyclyl containing 1-4 heteroatoms selected from N, O, and S, substituted with 0-4 $R^{2a}$;
$R^{2a}$ is independently, at each occurrence, hydrogen, halogen, $C_{1-6}$ alkyl, $C_{1-6}$ alkoxy, $C_{3-6}$ cycloalkyl, halo $C_{1-6}$ alkyl, hydroxy $C_{1-6}$ alkyl, $C_{5-8}$ aryl or a 5-7 membered heterocyclyl containing 1-4 heteroatoms selected from N, O, and S, said aryl or heterocyclyl substituted with 0-2 $R^a$;
$R^a$ is hydrogen, halogen or $C_{1-4}$ alkyl;
$R^3$ is P(O)—$(C_{1-4}$ alkyl$)_2$;
or a stereoisomer or pharmaceutically-acceptable salt thereof.

In a third aspect of the invention, there are provided compounds of the formula,

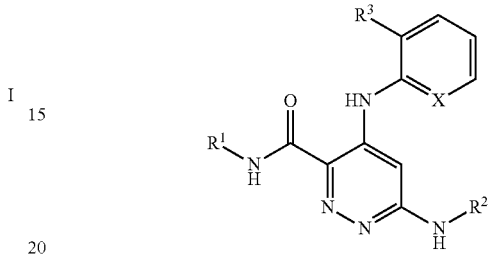

wherein:
X is —N— or —CH—;
$R^1$ is $CD_3$, $C_{1-3}$ alkyl or $C_{3-6}$ cycloalkyl;
$R^2$ is CO—$C_{3-6}$ cycloalkyl, $C_{5-8}$ aryl or a 5-7 membered heterocyclyl containing 1-4 heteroatoms selected from N, O, and S, substituted with 0-4 $R^{2a}$;
$R^{2a}$ is independently, at each occurrence, hydrogen, halogen, $C_{1-6}$ alkyl, $C_{1-6}$ alkoxy, $C_{3-6}$ cycloalkyl, halo $C_{1-6}$ alkyl, hydroxy $C_{1-6}$ alkyl, $C_{5-8}$ aryl or a 5-7 membered heterocyclyl containing 1-4 heteroatoms selected from N, O, and S, said aryl or heterocyclyl substituted with 0-2 $R^a$;
$R^a$ is hydrogen, halogen or $C_{1-4}$ alkyl;
$R^3$ is P(O)—$(C_{1-4}$ alkyl$)_2$;
or a stereoisomer or pharmaceutically-acceptable salt thereof.

In a fourth aspect of the invention, there are provided compounds of the formula

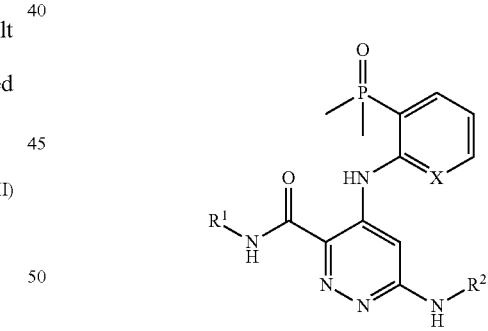

wherein:
X is —N— or —CH—;
$R^1$ is $CD_3$, $C_{1-3}$ alkyl or $C_{3-6}$ cycloalkyl;
$R^2$ is CO—$C_{3-6}$ cycloalkyl, $C_{5-8}$ aryl or a 5-7 membered heterocyclyl containing 1-4 heteroatoms selected from N, O, and S, substituted with 0-4 $R^{2a}$;
$R^{2a}$ is independently, at each occurrence, hydrogen, halogen, $C_{1-6}$ alkyl, $C_{1-6}$ alkoxy, $C_{3-6}$ cycloalkyl, halo $C_{1-6}$ alkyl, hydroxy $C_{1-6}$ alkyl, $C_{5-8}$ aryl or a 5-7 membered heterocyclyl containing 1-4 heteroatoms selected from N, O, and S, said aryl or heterocyclyl substituted with 0-2 $R^a$;
$R^a$ is hydrogen, halogen or $C_{1-4}$ alkyl;
or a stereoisomer or pharmaceutically-acceptable salt thereof.

In a fifth aspect of the invention, there are provided compounds as described above, wherein $R^1$ is $CD_3$ or $C_{1-3}$ alkyl;

$R^2$ is CO— $C_{3-6}$ cycloalkyl, $C_{5-8}$ aryl or a 5-7 membered heterocyclyl containing 1-4 heteroatoms selected from N, O, and S, substituted with 0-4 $R^{2a}$;

$R^{2a}$ is independently, at each occurrence, hydrogen, halogen, $C_{1-6}$ alkyl, $C_{1-6}$ alkoxy, $C_{3-6}$ cycloalkyl, halo $C_{1-6}$ alkyl, hydroxy $C_{1-6}$ alkyl, $C_{5-8}$ aryl or a 5-7 membered heterocyclyl containing 1-4 heteroatoms selected from N, O, and S, said aryl or heterocyclyl substituted with 0-2 $R^a$;

$R^a$ is hydrogen, halogen or $C_{1-4}$ alkyl;

or a stereoisomer or pharmaceutically-acceptable salt thereof.

In a sixth aspect of the invention, there are provided compounds as described above, wherein $R^1$ is $CD_3$;

$R^2$ is CO— $C_{3-6}$ cycloalkyl, $C_{5-8}$ aryl or a 5-7 membered heterocyclyl containing 1-4 heteroatoms selected from N, O, and S, substituted with 0-4 $R^{2a}$;

$R^{2a}$ is independently, at each occurrence, hydrogen, halogen, $C_{1-6}$ alkyl, $C_{1-6}$ alkoxy, $C_{3-6}$ cycloalkyl, halo $C_{1-6}$ alkyl, hydroxy $C_{1-6}$ alkyl, $C_{5-8}$ aryl or a 5-7 membered heterocyclyl containing 1-4 heteroatoms selected from N, O, and S, said aryl or heterocyclyl substituted with 0-2 $R^a$;

$R^a$ is hydrogen, halogen or $C_{1-4}$ alkyl;

or a stereoisomer or pharmaceutically-acceptable salt thereof.

In a seventh aspect of the invention, there are provided compounds of the formula,

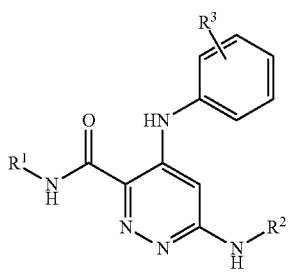

wherein:

$R^1$ is $CD_3$, $C_{1-3}$ alkyl or $C_{3-6}$ cycloalkyl;

$R^2$ is CO— $C_{3-6}$ cycloalkyl, $C_{5-8}$ aryl or a 5-7 membered heterocyclyl containing 1-4 heteroatoms selected from N, O, and S, substituted with 0-4 $R^{2a}$;

$R^{2a}$ is independently, at each occurrence, hydrogen, halogen, $C_{1-6}$ alkyl, $C_{1-6}$ alkoxy, $C_{3-6}$ cycloalkyl, halo $C_{1-6}$ alkyl, hydroxy $C_{1-6}$ alkyl, $C_{5-8}$ aryl or a 5-7 membered heterocyclyl containing 1-4 heteroatoms selected from N, O, and S, said aryl or heterocyclyl substituted with 0-2 $R^a$;

$R^a$ is hydrogen, halogen or $C_{1-4}$ alkyl;

$R^3$ is P(O)—$(C_{1-4}$ alkyl$)_2$;

or a stereoisomer or pharmaceutically-acceptable salt thereof.

In an eighth aspect of the invention, there are provided compounds of the formula,

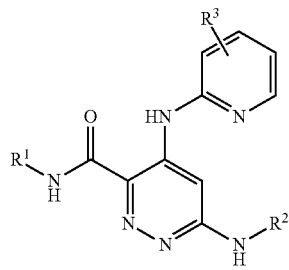

wherein:

$R^1$ is $CD_3$, $C_{1-3}$ alkyl or $C_{3-6}$ cycloalkyl;

$R^2$ is CO— $C_{3-6}$ cycloalkyl, $C_{5-8}$ aryl or a 5-7 membered heterocyclyl containing 1-4 heteroatoms selected from N, O, and S, substituted with 0-4 $R^{2a}$;

$R^{2a}$ is independently, at each occurrence, hydrogen, halogen, $C_{1-6}$ alkyl, $C_{1-6}$ alkoxy, $C_{3-6}$ cycloalkyl, halo $C_{1-6}$ alkyl, hydroxy $C_{1-6}$ alkyl, $C_{5-8}$ aryl or a 5-7 membered heterocyclyl containing 1-4 heteroatoms selected from N, O, and S, said aryl or heterocyclyl substituted with 0-2 $R^a$;

$R^a$ is hydrogen, halogen or $C_{1-4}$ alkyl;

$R^3$ is P(O)—$(C_{1-4}$ alkyl$)_2$;

or a stereoisomer or pharmaceutically-acceptable salt thereof.

In another aspect, there is provided a compound selected from the exemplified examples within the scope of the first aspect, or a pharmaceutically acceptable salt, tautomer or stereoisomer thereof.

In another aspect, there is provided a compound selected from any subset list of compounds within the scope of any of the above aspects.

In another embodiment, there is provided a pharmaceutical composition comprising one or more compounds of formula I and a pharmaceutically acceptable carrier or diluent.

The present invention is also directed to pharmaceutical compositions useful in treating diseases associated with the modulation of IL-12, IL-23 and/or IFNα by acting on Tyk-2 to cause signal transduction inhibition, comprising compounds of formula I, or pharmaceutically-acceptable salts thereof, and pharmaceutically-acceptable carriers or diluents.

The invention further relates to methods of treating diseases associated with the modulation of IL-12, IL-23, and/or IFNα, comprising administering to a patient in need of such treatment a therapeutically-effective amount of a compound according to formula I.

The present invention also provides a method for treating proliferative, metabolic, allergic, autoimmune and inflammatory diseases (or use of the compounds of the present invention for the manufacture of a medicament for the treatment of these diseases), comprising administering to a host in need of such treatment a therapeutically effective amount of at least one of the compounds of the present invention.

The present invention also provides a method of treating an inflammatory or autoimmune disease (or use of the compounds of the present invention for the manufacture of a medicament for the treatment of these diseases) comprising administering to a patient in need of such treatment a therapeutically-effective amount of a compound of Formula I.

The present invention also provides a method for treating a disease (or use of the compounds of the present invention for the manufacture of a medicament for the treatment of these diseases), comprising administering to a patient in need of such treatment a therapeutically-effective amount of a compound of Formula I, wherein the disease is rheumatoid arthritis, multiple sclerosis, systemic lupus erythematosus (SLE), lupus nephritis, cutaneous lupus, inflammatory bowel disease, psoriasis, Crohn's Disease, psoriatic arthritis, Sjögren's syndrome, systemic scleroderma, ulcerative colitis, Graves' disease, discoid lupus erythematosus, adult onset Stills, systemic onset juvenile idiopathic arthritis, gout, gouty arthritis, type 1 diabetes, insulin dependent diabetes mellitus, sepsis, septic shock, Shigellosis, pancreatitis (acute or chronic), glomerulonephritis, autoimmune gastritis, diabetes, autoimmune hemolytic anemia, autoimmune neutropenia, thrombocytopenia, atopic dermatitis, myasthenia gravis, pancreatitis (acute or chronic), ankylosing spondylitis, pemphigus vulgaris, Goodpasture's disease, antiphospholipid syndrome, idiopathic thrombocytopenia, ANCA-associated vasculitis, pemphigus, Kawasaki disease, Chronic Inflammatory Demyelinating Polyneuropathy (CIDP), dermatomyositis, polymyositis, uveitis, Guillain-Barre syndrome, autoimmune pulmonary inflammation, autoimmune thyroiditis, autoimmune inflammatory eye disease, and chronic demyelinating polyneuropathy.

The present invention also provides a method of treating an inflammatory or autoimmune disease (or use of the compounds of the present invention for the manufacture of a medicament for the treatment of said diseases), comprising administering to a patient in need of such treatment a therapeutically-effective amount of a compound of Formula I, wherein the disease is selected from systemic lupus erythematosus (SLE), lupus nephritis, cutaneous lupus, Crohn's Disease, ulcerative colitis, type 1 diabetes, psoriasis, rheumatoid arthritis, systemic onset juvenile idiopathic arthritis, ankylosing spondylitis, and multiple sclerosis.

The present invention also provides a method for treating a rheumatoid arthritis (or use of the compounds of the present invention for the manufacture of a medicament for the treatment of rheumatoid arthritis, comprising administering to a patient in need of such treatment a therapeutically-effective amount of a compound of Formula I.

In addition, the present invention also provides a method of treating a condition (or use of the compounds of the present invention for the manufacture of a medicament for the treatment of these conditions) comprising administering to a patient in need of such treatment a therapeutically-effective amount of a compound of Formula I, wherein the condition is selected from acute myelogenous leukemia, chronic myelogenous leukemia, metastatic melanoma, Kaposi's sarcoma, multiple myeloma, solid tumors, ocular neovasculization, and infantile haemangiomas, B cell lymphoma, systemic lupus erythematosus (SLE), rheumatoid arthritis, psoriatic arthritis, multiple vasculitides, idiopathic thrombocytopenic purpura (ITP), myasthenia gravis, allergic rhinitis, multiple sclerosis (MS), transplant rejection, Type I diabetes, membranous nephritis, inflammatory bowel disease, autoimmune hemolytic anemia, autoimmune thyroiditis, cold and warm agglutinin diseases, Evans syndrome, hemolytic uremic syndrome/thrombotic thrombocytopenic purpura (HUS/TTP), sarcoidosis, Sjögren's syndrome, peripheral neuropathies, pemphigus vulgaris and asthma.

The present invention also provides a method of treating a IL-12, IL-23, and/or IFNα mediated disease (or use of the compounds of the present invention for the manufacture of a medicament for the treatment of these diseases), comprising administering to a patient in need of such treatment a therapeutically-effective amount of a compound of formula I.

The present invention also provides a method of treating a IL-12, IL-23 and/or IFNα mediated disease (or use of the compounds of the present invention for the manufacture of a medicament for the treatment of these diseases), comprising administering to a patient in need of such treatment a therapeutically-effective amount of a compound of formula I, wherein the IL-12, IL-23 and/or IFNα mediated disease is a disease modulated by IL-12, IL-23 and/or IFNα.

The present invention also provides a method of treating diseases, comprising administering to a patient in need of such treatment a therapeutically-effective amount of a compound of formula I in combination with other therapeutic agents.

The present invention also provides the compounds of the present invention for use in therapy.

In another embodiment, compounds of formula I are selected from exemplified compounds or combinations of exemplified compounds or other embodiments herein.

The present invention may be embodied in other specific forms without departing from the spirit or essential attributes thereof. This invention encompasses all combinations of preferred aspects and/or embodiments of the invention noted herein. It is understood that any and all embodiments of the present invention may be taken in conjunction with any other embodiment or embodiments to describe additional more preferred embodiments. It is also to be understood that each individual element of the preferred embodiments is its own independent preferred embodiment. Furthermore, any element of an embodiment is meant to be combined with any and all other elements from any embodiment to describe an additional embodiment.

DEFINITIONS

The following are definitions of terms used in this specification and appended claims. The initial definition provided for a group or term herein applies to that group or term throughout the specification and claims, individually or as part of another group, unless otherwise indicated.

Compounds of this invention may have one or more asymmetric centers. Unless otherwise indicated, all chiral (enantiomeric and diastereomeric) and racemic forms of compounds of the present invention are included in the present invention. Many geometric isomers of olefins, C=N double bonds, and the like can also be present in the compounds, and all such stable isomers are contemplated in the present invention. Cis- and trans-geometric isomers of the compounds of the present invention are described and may be isolated as a mixture of isomers or as separated isomeric forms. The present compounds can be isolated in optically active or racemic forms. It is well known in the art how to prepare optically active forms, such as by resolution of racemic forms or by synthesis from optically active starting materials. All chiral, (enantiomeric and diastereomeric) and racemic forms and all geometric isomeric forms of a structure are intended, unless the specific stereochemistry or isomer form is specifically indicated.

When any variable (e.g., $R^3$) occurs more than one time in any constituent or formula for a compound, its definition at each occurrence is independent of its definition at every other occurrence. Thus, for example, if a group is shown to be substituted with 0-2 $R^3$, then said group may optionally be substituted with up to two $R^3$ groups and $R^3$ at each occurrence is selected independently from the definition of $R^3$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

In cases wherein there are nitrogen atoms (e.g., amines) on compounds of the present invention, these can be converted to N-oxides by treatment with an oxidizing agent (e.g., MCPBA and/or hydrogen peroxides) to afford other compounds of this invention. Thus, all shown and claimed nitrogen atoms are considered to cover both the shown nitrogen and its N-oxide (N→O) derivative.

In accordance with a convention used in the art,

is used in structural formulas herein to depict the bond that is the point of attachment of the moiety or substituent to the core or backbone structure.

A dash "-" that is not between two letters or symbols is used to indicate a point of attachment for a substituent. For example, —CONH$_2$ is attached through the carbon atom.

The term "optionally substituted" in reference to a particular moiety of the compound of Formula I (e.g., an optionally substituted heteroaryl group) refers to a moiety having 0, 1, 2, or more substituents. For example, "optionally substituted alkyl" encompasses both "alkyl" and "substituted alkyl" as defined below. It will be understood by those skilled in the art, with respect to any group containing one or more substituents, that such groups are not intended to introduce any substitution or substitution patterns that are sterically impractical, synthetically non-feasible and/or inherently unstable.

As used herein, the term "at least one chemical entity" is interchangeable with the term "a compound".

As used herein, the term "alkyl" or "alkylene" is intended to include both branched and straight-chain saturated aliphatic hydrocarbon groups having the specified number of carbon atoms. For example, "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$-$C_6$ alkyl" denotes alkyl having 1 to 6 carbon atoms. Alkyl groups can be unsubstituted or substituted so that one or more of its hydrogens are replaced by another chemical group. Example alkyl groups include, but are not limited to, methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like.

"Alkenyl" or "alkenylene" is intended to include hydrocarbon chains of either straight or branched configuration and having one or more double carbon-carbon bonds that may occur in any stable point along the chain. For example, "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3-pentenyl, 4-pentenyl, 2-hexenyl, 3-hexenyl, 4-hexenyl, 5-hexenyl, 2-methyl-2-propenyl, 4-methyl-3-pentenyl, and the like.

"Alkynyl" or "alkynylene" is intended to include hydrocarbon chains of both straight or branched configuration and having one or more triple carbon-carbon bonds that may occur in any stable point along the chain. For example, "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, hexynyl and the like.

One skilled in the field will understand that, when the designation "$CO_2$" is used herein, this is intended to refer to the group

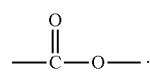

When the term "alkyl" is used together with another group, such as in "arylalkyl", this conjunction defines with more specificity at least one of the substituents that the substituted alkyl will contain. For example, "arylalkyl" refers to a substituted alkyl group as defined above where at least one of the substituents is an aryl, such as benzyl. Thus, the term aryl($C_{0-4}$)alkyl includes a substituted lower alkyl having at least one aryl substituent and also includes an aryl directly bonded to another group, i.e., aryl($C_0$)alkyl. The term "heteroarylalkyl" refers to a substituted alkyl group as defined above where at least one of the substituents is a heteroaryl.

When reference is made to a substituted alkenyl, alkynyl, alkylene, alkenylene, or alkynylene group, these groups are substituted with one to three substituents as defined above for substituted alkyl groups.

The term "alkoxy" refers to an oxygen atom substituted by alkyl or substituted alkyl, as defined herein. For example, the term "alkoxy" includes the group —O—$C_{1-6}$alkyl such as methoxy, ethoxy, propoxy, isopropoxy, n-butoxy, sec-butoxy, tert-butoxy, pentoxy, 2-pentyloxy, isopentoxy, neopentoxy, hexoxy, 2-hexoxy, 3-hexoxy, 3-methylpentoxy, and the like. "Lower alkoxy" refers to alkoxy groups having one to four carbons.

It should be understood that the selections for all groups, including for example, alkoxy, thioalkyl, and aminoalkyl, will be made by one skilled in the field to provide stable compounds.

The term "substituted", as used herein, means that any one or more hydrogens on the designated atom or group is replaced with a selection from the indicated group, provided that the designated atom's normal valence is not exceeded. When a substituent is oxo, or keto, (i.e., =O) then 2 hydrogens on the atom are replaced. Keto substituents are not present on aromatic moieties. Unless otherwise specified, substituents are named into the core structure. For example, it is to be understood that when (cycloalkyl)alkyl is listed as a possible substituent, the point of attachment of this substituent to the core structure is in the alkyl portion. Ring double bonds, as used herein, are double bonds that are formed between two adjacent ring atoms (e.g., C=C, C=N, or N=N).

Combinations of substituents and/or variables are permissible only if such combinations result in stable compounds or useful synthetic intermediates. A stable compound or stable structure is meant to imply a compound that is sufficiently robust to survive isolation from a reaction mixture to a useful degree of purity, and subsequent formulation into an efficacious therapeutic agent. It is preferred that the presently recited compounds do not contain a N-halo, S(O)₂H, or S(O)H group.

The term "cycloalkyl" refers to cyclized alkyl groups, including mono-, bi- or poly-cyclic ring systems. $C_{3-7}$ cycloalkyl is intended to include $C_3$, $C_4$, $C_5$, $C_6$, and $C_7$ cycloalkyl groups. Example cycloalkyl groups include, but are not limited to, cyclopropyl, cyclobutyl, cyclopentyl, cyclohexyl, norbornyl, and the like. As used herein, "carbocycle" or "carbocyclic residue" is intended to mean any stable 3-, 4-, 5-, 6-, or 7-membered monocyclic or bicyclic or 7-, 8-, 9-, 10-, 11-, 12-, or 13-membered bicyclic or tricyclic ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane, [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, and phenyl. When the term "carbocycle" is used, it is intended to include "aryl". A bridged ring occurs when one or more carbon atoms link two non-adjacent carbon atoms. Preferred bridges are one or two carbon atoms. It is noted that a bridge always converts a monocyclic ring into a bicyclic ring. When a ring is bridged, the substituents recited for the ring may also be present on the bridge.

The term "aryl" refers to monocyclic or bicyclic aromatic hydrocarbon groups having 6 to 12 carbon atoms in the ring portion, such as phenyl, and naphthyl groups, each of which may be substituted.

Accordingly, in compounds of formula I, the term "cycloalkyl" includes cyclopropyl, cyclobutyl, cyclopentyl, cyclohexyl, cycloheptyl, bicyclooctyl, etc., as well as the following ring systems:

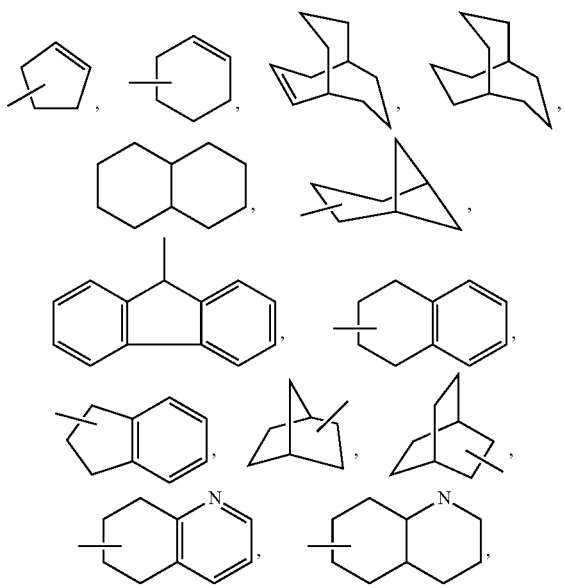

and the like, which optionally may be substituted at any available atoms of the ring(s). Preferred cycloalkyl groups include cyclopropyl, cyclopentyl, cyclohexyl, and

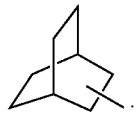

The term "halo" or "halogen" refers to chloro, bromo, fluoro and iodo.

The term "haloalkyl" means a substituted alkyl having one or more halo substituents. For example, "haloalkyl" includes mono, bi, and trifluoromethyl.

The term "haloalkoxy" means an alkoxy group having one or more halo substituents. For example, "haloalkoxy" includes $OCF_3$.

Thus, examples of aryl groups include:

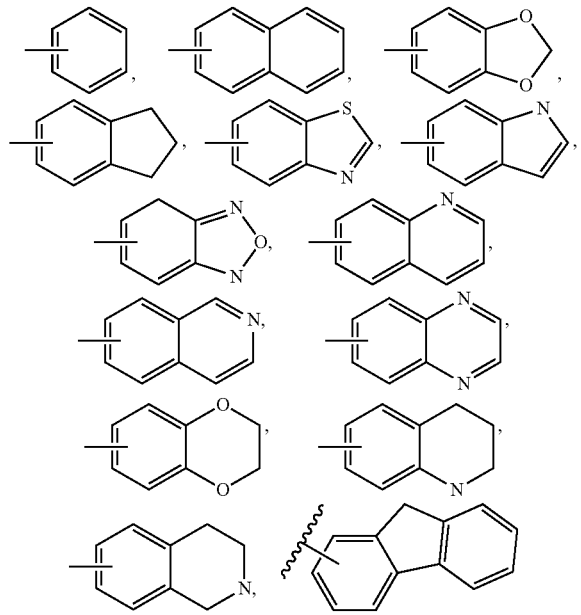

and the like, which optionally may be substituted at any available carbon or nitrogen atom. A preferred aryl group is optionally-substituted phenyl.

The terms "heterocycle", "heterocycloalkyl", "heterocyclo", "heterocyclic", or "heterocyclyl" may be used interchangeably and refer to substituted and unsubstituted 3- to 7-membered monocyclic groups, 7- to 11-membered bicyclic groups, and 10- to 15-membered tricyclic groups, in which at least one of the rings has at least one heteroatom (O, S or N), said heteroatom containing ring preferably having 1, 2, or 3 heteroatoms selected from O, S, and N. Each ring of such a group containing a heteroatom can contain one or two oxygen or sulfur atoms and/or from one to four nitrogen atoms provided that the total number of heteroatoms in each ring is four or less, and further provided that the ring contains at least one carbon atom. The nitrogen and sulfur atoms may optionally be oxidized and the nitrogen atoms may optionally be quaternized. The fused rings completing the bicyclic and tricyclic groups may contain only carbon atoms and may be saturated, partially saturated, or fully unsaturated. The heterocyclo group may be attached at any available nitrogen or carbon atom. As used herein the terms "heterocycle", "heterocycloalkyl", "heterocyclo", "heterocyclic", and "heterocyclyl" include "heteroaryl" groups, as defined below.

In addition to the heteroaryl groups described below, exemplary monocyclic heterocyclyl groups include azetidinyl, pyrrolidinyl, oxetanyl, imidazolinyl, oxazolidinyl, isoxazolinyl, thiazolidinyl, isothiazolidinyl, tetrahydrofuranyl, piperidyl, piperazinyl, 2-oxopiperazinyl, 2-oxopiperidyl, 2-oxopyrrolodinyl, 2-oxoazepinyl, azepinyl, 1-pyridonyl, 4-piperidonyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl and the like. Exemplary bicyclic heterocyclo groups include quinuclidinyl. Additional monocyclic heterocyclyl groups include

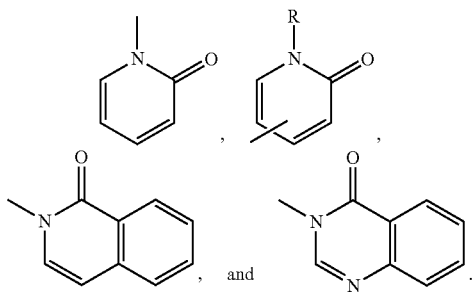

The term "heteroaryl" refers to substituted and unsubstituted aromatic 5- or 6-membered monocyclic groups, 9- or 10-membered bicyclic groups, and 11- to 14-membered tricyclic groups which have at least one heteroatom (O, S or N) in at least one of the rings, said heteroatom-containing ring preferably having 1, 2, or 3 heteroatoms selected from O, S, and N. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. As valence allows, if said further ring is cycloalkyl or heterocyclo it is additionally optionally substituted with =O (oxo).

Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl and the like.

Exemplary bicyclic heteroaryl groups include indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridyl, dihydroisoindolyl, tetrahydroquinolinyl and the like.

Exemplary tricyclic heteroaryl groups include carbazolyl, benzindolyl, phenanthrollinyl, acridinyl, phenanthridinyl, xanthenyl and the like.

In compounds of formula I, preferred heteroaryl groups include:

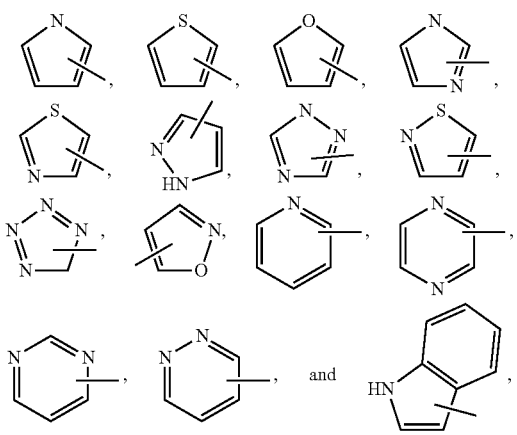

and the like, which optionally may be substituted at any available carbon or nitrogen atom.

Unless otherwise indicated, when reference is made to a specifically-named aryl (e.g., phenyl), cycloalkyl (e.g., cyclohexyl), heterocyclo (e.g., pyrrolidinyl, piperidinyl, and morpholinyl) or heteroaryl (e.g., tetrazolyl, imidazolyl, pyrazolyl, triazolyl, thiazolyl, and furyl) the reference is intended to include rings having 0 to 3, preferably 0 to 2, substituents selected from those recited above for the aryl, cycloalkyl, heterocyclo and/or heteroaryl groups, as appropriate.

The term "carbocyclyl" or "carbocyclic" refers to a saturated or unsaturated monocyclic or bicyclic ring in which all atoms of all rings are carbon. Thus, the term includes cycloalkyl and aryl rings. Monocyclic carbocycles have 3 to 6 ring atoms, still more typically 5 or 6 ring atoms. Bicyclic carbocycles have 7 to 12 ring atoms, e.g., arranged as a bicyclo [4,5], [5,5], [5,6] or [6,6] system, or 9 or 10 ring atoms arranged as a bicyclo [5,6] or [6,6] system. Examples of mono- and bicyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, phenyl and naphthyl. The carbocyclic ring may be substituted in which case the substituents are selected from those recited above for cycloalkyl and aryl groups.

The term "heteroatoms" shall include oxygen, sulfur and nitrogen.

When the term "unsaturated" is used herein to refer to a ring or group, the ring or group may be fully unsaturated or partially unsaturated.

Throughout the specification, groups and substituents thereof may be chosen by one skilled in the field to provide stable moieties and compounds and compounds useful as pharmaceutically-acceptable compounds and/or intermediate compounds useful in making pharmaceutically-acceptable compounds.

The compounds of formula I may exist in a free form (with no ionization) or can form salts which are also within the scope of this invention. Unless otherwise indicated, reference to an inventive compound is understood to include reference to the free form and to salts thereof. The term "salt(s)" denotes acidic and/or basic salts formed with inorganic and/or organic acids and bases. In addition, the term "salt(s)" may include zwitterions (inner salts), e.g., when a compound of formula I, contains both a basic moiety, such as an amine or a pyridine or imidazole ring, and an acidic moiety, such as a carboxylic acid. Pharmaceutically acceptable (i.e., non-toxic, physiologically acceptable) salts are preferred, such as, for example, acceptable metal and amine salts in which the cation does not contribute significantly to the toxicity or biological activity of the salt. However, other salts may be useful, e.g., in isolation or purification steps which may be employed during preparation, and thus, are contemplated within the scope of the invention. Salts of the compounds of the formula I may be formed, for example, by reacting a compound of the formula I with an amount of acid or base, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts include ammonium salts, alkali metal salts such as sodium, lithium, and potassium salts; alkaline earth metal salts such as calcium and magnesium salts; barium, zinc, and aluminum salts; salts with organic bases (for example, organic amines) such as trialkylamines such as triethylamine, procaine, dibenzylamine, N-benzyl-β-phenethylamine, 1-ephenamine, N,N'-dibenzylethylenediamine, dehydroabietylamine, N-ethylpiperidine, benzylamine, dicyclohexylamine or similar pharmaceutically acceptable amines and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others. Preferred salts include monohydrochloride, hydrogensulfate, methanesulfonate, phosphate or nitrate salts.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically-acceptable salts" refer to derivatives of the disclosed compounds wherein the parent compound is modified by making acid or base salts thereof. Examples of pharmaceutically-acceptable salts include, but are not limited to, mineral or organic acid salts of basic groups such as amines; and alkali or organic salts of acidic groups such as carboxylic acids. The pharmaceutically-acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically-acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 18th Edition, Mack Publishing Company, Easton, Pa. (1990), the disclosure of which is hereby incorporated by reference.

All stereoisomers of the compounds of the instant invention are contemplated, either in admixture or in pure or substantially pure form. Stereoisomers may include compounds which are optical isomers through possession of one or more chiral atoms, as well as compounds which are optical isomers by virtue of limited rotation about one or more bonds (atropisomers). The definition of compounds according to the invention embraces all the possible stereoisomers and their mixtures. It very particularly embraces the racemic forms and the isolated optical isomers having the specified activity. The racemic forms can be resolved by physical methods, such as, for example, fractional crystallization, separation or crystallization of diastereomeric derivatives or separation by chiral column chromatography. The individual optical isomers can be obtained from the racemates from the conventional methods, such as, for example, salt formation with an optically active acid followed by crystallization.

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}$C and $^{14}$C. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

Prodrugs and solvates of the inventive compounds are also contemplated. The term "prodrug" denotes a compound which, upon administration to a subject, undergoes chemical conversion by metabolic or chemical processes to yield a compound of the formula I, and/or a salt and/or solvate thereof. Any compound that will be converted in vivo to provide the bioactive agent (i.e., the compound for formula I) is a prodrug within the scope and spirit of the invention. For example, compounds containing a carboxy group can form physiologically hydrolyzable esters which serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkylbenzyl, 4-methoxybenzyl, indanyl, phthalyl, methoxymethyl, $C_{1-6}$alkanoyloxy-$C_{1-6}$alkyl, e.g., acetoxymethyl, pivaloyloxymethyl or propionyloxymethyl, $C_{1-6}$alkoxycarbonyloxy-$C_{1-6}$alkyl, e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl and other well known physiologically hydrolyzable esters used, for example, in the penicillin and cephalosporin arts. Such esters may be prepared by conventional techniques known in the art.

Various forms of prodrugs are well known in the art. For examples of such prodrug derivatives, see:
a) Bundgaard, H., ed., Design of Prodrugs, Elsevier (1985), and Widder, K. et al., eds., *Methods in Enzymology*, 112:309-396, Academic Press (1985);
b) Bundgaard, H., Chapter 5, "Design and Application of Prodrugs", Krosgaard-Larsen, P. et al., eds., *A Textbook of Drug Design and Development*, pp. 113-191, Harwood Academic Publishers (1991); and
c) Bundgaard, H., *Adv. Drug Deliv. Rev.*, 8:1-38 (1992), each of which is incorporated herein by reference.

Compounds of the formula I and salts thereof may exist in their tautomeric form, in which hydrogen atoms are transposed to other parts of the molecules and the chemical bonds between the atoms of the molecules are consequently rearranged. It should be understood that the all tautomeric forms, insofar as they may exist, are included within the invention. Additionally, inventive compounds may have trans- and cis-isomers.

It should further be understood that solvates (e.g., hydrates) of the compounds of Formula I are also with the scope of the present invention. Methods of solvation are generally known in the art.

UTILITY

The compounds of the invention modulate IL-23-stimulated and IFNα-stimulated cellular functions, including gene transcription. Other types of cellular functions that may be modulated by the compounds of the instant invention include, but are not limited to, IL-12-stimulated responses.

Accordingly, compounds of formula I have utility in treating conditions associated with the modulation of the function of IL-23 or IFNα, and particularly the selective inhibition of function of IL-23, IL-12 and/or IFNα, by acting on Tyk2 to mediate signal transduction. Such conditions include IL-23-, IL-12-, or IFNα-associated diseases in which pathogenic mechanisms are mediated by these cytokines.

As used herein, the terms "treating" or "treatment" encompass the treatment of a disease state in a mammal, particularly in a human, and include: (a) preventing or delaying the occurrence of the disease state in a mammal, in particular, when such mammal is predisposed to the disease state but has not yet been diagnosed as having it; (b) inhibiting the disease state, i.e., arresting its development; and/or (c) achieving a full or partial reduction of the symptoms or disease state, and/or alleviating, ameliorating, lessening, or curing the disease or disorder and/or its symptoms.

In view of their activity as modulators of IL-23-, IL-12 and IFNα-stimulated cellular responses, compounds of Formula I are useful in treating IL-23-, IL-12- or IFNα-associated diseases including, but not limited to, inflammatory diseases such as Crohn's disease, ulcerative colitis, asthma, graft versus host disease, allograft rejection, chronic obstructive pulmonary disease; autoimmune diseases such as Graves' disease, rheumatoid arthritis, systemic lupus erythematosis, cutaneous lupus, lupus nephritis, discoid lupus erythematosus, psoriasis; auto-inflammatory diseases including CAPS, TRAPS, FMF, adult onset stills, systemic onset juvenile idiopathic arthritis, gout, gouty arthritis; metabolic diseases including type 2 diabetes, atherosclerosis, myocardial infarction; destructive bone disorders such as bone resorption disease, osteoarthritis, osteoporosis, multiple myeloma-related bone disorder; proliferative disorders such as acute myelogenous leukemia, chronic myelogenous leukemia; angiogenic disorders such as angiogenic disorders including solid tumors, ocular neovasculization, and infantile haemangiomas; infectious diseases such as sepsis, septic shock, and Shigellosis; neurodegenerative diseases such as Alzheimer's disease, Parkinson's disease, cerebral ischemias or neurodegenerative disease caused by traumatic injury, oncologic and viral diseases such as metastatic melanoma, Kaposi's sarcoma, multiple myeloma, and HIV infection and CMV retinitis, AIDS, respectively.

More particularly, the specific conditions or diseases that may be treated with the inventive compounds include, without limitation, pancreatitis (acute or chronic), asthma, allergies, adult respiratory distress syndrome, chronic obstructive pulmonary disease, glomerulonephritis, rheumatoid arthritis, systemic lupus erythematosis, cutaneous lupus, lupus nephritis, discoid lupus erythematosus, scleroderma, chronic thyroiditis, Graves' disease, autoimmune gastritis, diabetes, autoimmune hemolytic anemia, autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, graft vs. host disease, inflammatory reaction induced by endotoxin, tuberculosis, atherosclerosis, muscle degeneration, cachexia, psoriatic arthritis, Reiter's syndrome, gout, traumatic arthritis, rubella arthritis, acute synovitis, pancreatic β-cell disease; diseases characterized by massive neutrophil infiltration; rheumatoid spondylitis, gouty arthritis and other arthritic conditions, cerebral malaria, chronic pulmonary inflammatory disease, silicosis, pulmonary sarcoidosis, bone resorption disease, allograft rejections, fever and myalgias due to infection, cachexia secondary to infection, keloid formation, scar tissue formation, ulcerative colitis, pyresis, influenza, osteoporosis, osteoarthritis, acute myelogenous leukemia, chronic myelogenous leukemia, metastatic melanoma, Kaposi's sarcoma, multiple myeloma, sepsis, septic shock, and Shigellosis; Alzheimer's disease, Parkinson's disease, cerebral ischemias or neurodegenerative disease caused by traumatic injury; angiogenic disorders including solid tumors, ocular neovasculization, and infantile haemangiomas; viral diseases including acute hepatitis infection (including hepatitis A, hepatitis B and hepatitis C), HIV infection and CMV retinitis, AIDS, ARC or malignancy, and herpes; stroke, myocardial ischemia, ischemia in stroke heart attacks, organ hyposia [should this be hypoxia], vascular hyperplasia, cardiac and renal reperfusion injury, thrombosis, cardiac hypertrophy, thrombin-induced platelet aggregation, endotoxemia and/or toxic shock syndrome, conditions associated with prostaglandin endoperoxidase syndase-2, and pemphigus vulgaris. Preferred methods of treatment are those wherein the condition is selected from Crohn's disease, ulcerative colitis, allograft rejection, rheumatoid arthritis, psoriasis, ankylosing spondylitis, psoriatic arthritis, and pemphigus vulgaris. Alternatively preferred methods of treatment are those wherein the condition is selected from ischemia reperfusion injury, including cerebral ischemia reperfusions injury arising from stroke and cardiac ischemia reperfusion injury arising from myocardial infarction. Another preferred method of treatment is one in which the condition is multiple myeloma.

When the terms "IL-23-, IL-12- and/or IFNα-associated condition" or "IL-23-, IL-12- and/or IFNα-associated disease or disorder" are used herein, each is intended to encompass all of the conditions identified above as if repeated at length, as well as any other condition that is affected by IL-23, IL-12 and/or IFNα.

The present invention thus provides methods for treating such conditions, comprising administering to a subject in need thereof a therapeutically-effective amount of at least one compound of Formula I or a salt thereof "Therapeutically effective amount" is intended to include an amount of a compound of the present invention that is effective when administered alone or in combination to inhibit IL-23, IL-12 and/or IFNα function and/or treat diseases.

The methods of treating IL-23-, IL-12 and/or IFNα-associated conditions may comprise administering compounds of Formula I alone or in combination with each other and/or other suitable therapeutic agents useful in treating such conditions. Accordingly, "therapeutically effective amount" is also intended to include an amount of the combination of compounds claimed that is effective to inhibit IL-23, IL-12 and/or IFNα function and/or treat diseases associated with IL-23, IL-12 and/or IFNα.

Exemplary of such other therapeutic agents include corticosteroids, rolipram, calphostin, cytokine-suppressive anti-inflammatory drugs (CSAIDs), Interleukin-10, glucocorticoids, salicylates, nitric oxide, and other immunosuppressants; nuclear translocation inhibitors, such as deoxyspergualin (DSG); non-steroidal anti-inflammatory drugs (NSAIDs) such as ibuprofen, celecoxib and rofecoxib; steroids such as prednisone or dexamethasone; antiviral agents such as abacavir; antiproliferative agents such as methotrexate, leflunomide, FK506 (tacrolimus, PROGRAF®); anti-malarials such as hydroxychloroquine; cytotoxic drugs such as azathiprine and cyclophosphamide; TNF-α inhibitors such as tenidap, anti-TNF antibodies or soluble TNF receptor, and rapamycin (sirolimus or RAPAMUNE®) or derivatives thereof.

The above other therapeutic agents, when employed in combination with the compounds of the present invention, may be used, for example, in those amounts indicated in the *Physicians' Desk Reference* (PDR) or as otherwise determined by one of ordinary skill in the art. In the methods of the present invention, such other therapeutic agent(s) may be administered prior to, simultaneously with, or following the administration of the inventive compounds. The present invention also provides pharmaceutical compositions capable of treating IL-23-, IL-12- or IFNα-associated conditions by inhibiting Tyk2-mediated signal transduction, including IL-23-, IL-12- and/or IFNα-mediated diseases, as described above.

FORMULATIONS/PHARMACEUTICAL COMPOSITIONS

The inventive compositions may contain other therapeutic agents as described above and may be formulated, for example, by employing conventional solid or liquid vehicles or diluents, as well as pharmaceutical additives of a type appropriate to the mode of desired administration (e.g., excipients, binders, preservatives, stabilizers, flavors, etc.) according to techniques such as those well known in the art of pharmaceutical formulation.

Accordingly, the present invention further includes compositions comprising one or more compounds of Formula I and a pharmaceutically acceptable carrier.

A "pharmaceutically acceptable carrier" refers to media generally accepted in the art for the delivery of biologically active agents to animals, in particular, mammals. Pharmaceutically acceptable carriers are formulated according to a number of factors well within the purview of those of ordinary skill in the art. These include without limitation the type and nature of the active agent being formulated; the subject to which the agent-containing composition is to be administered; the intended route of administration of the composition; and, the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences,* 17th Edition (1985), which is incorporated herein by reference in its entirety.

The compounds of Formula I may be administered by any means suitable for the condition to be treated, which may depend on the need for site-specific treatment or quantity of drug to be delivered. Topical administration is generally preferred for skin-related diseases, and systematic treatment preferred for cancerous or pre-cancerous conditions, although other modes of delivery are contemplated. For example, the compounds may be delivered orally, such as in the form of tablets, capsules, granules, powders, or liquid formulations including syrups; topically, such as in the form of solutions, suspensions, gels or ointments; sublingually; bucally; parenterally, such as by subcutaneous, intravenous, intramuscular or intrasternal injection or infusion techniques (e.g., as sterile injectable aq. or non-aq. solutions or suspensions); nasally such as by inhalation spray; topically, such as in the form of a cream or ointment; rectally such as in the form of suppositories; or liposomally. Dosage unit formulations containing non-toxic, pharmaceutically acceptable vehicles or diluents may be administered. The compounds may be administered in a form suitable for immediate release or extended release. Immediate release or extended release may be achieved with suitable pharmaceutical compositions or, particularly in the case of extended release, with devices such as subcutaneous implants or osmotic pumps.

Exemplary compositions for topical administration include a topical carrier such as PLASTIBASE® (mineral oil gelled with polyethylene).

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The inventive compounds may also be orally delivered by sublingual and/or buccal administration, e.g., with molded, compressed, or freeze-dried tablets. Exemplary compositions may include fast-dissolving diluents such as mannitol, lactose, sucrose, and/or cyclodextrins. Also included in such formulations may be high molecular weight excipients such as celluloses (AVICEL®) or polyethylene glycols (PEG); an excipient to aid mucosal adhesion such as hydroxypropyl cellulose (HPC), hydroxypropyl methyl cellulose (HPMC), sodium carboxymethyl cellulose (SCMC), and/or maleic anhydride copolymer (e.g., GANTREZ®); and agents to control release such as polyacrylic copolymer (e.g., CARBOPOL 934®). Lubricants, glidants, flavors, coloring agents and stabilizers may also be added for ease of fabrication and use.

Exemplary compositions for nasal aerosol or inhalation administration include solutions which may contain, for example, benzyl alcohol or other suitable preservatives, absorption promoters to enhance absorption and/or bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, suitable non-irritating excipients, such as cocoa butter, synthetic glyceride esters or polyethylene glycols, which are solid at ordinary temperatures but liquefy and/or dissolve in the rectal cavity to release the drug.

The therapeutically-effective amount of a compound of the present invention may be determined by one of ordinary skill in the art, and includes exemplary dosage amounts for a mammal of from about 0.05 to 1000 mg/kg; 1-1000 mg/kg; 1-50 mg/kg; 5-250 mg/kg; 250-1000 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats, horses, and the like. Thus, when the term "patient" is used herein, this term is intended to include all subjects, most preferably mammalian species that are affected by modulation of IL-23, IL-12 and/or IFNα-mediated functions.

METHODS OF PREPARATION

The compounds of the present invention may be synthesized by many methods available to those skilled in the art of organic chemistry. General synthetic schemes for preparing compounds of the present invention are described below. These schemes are illustrative and are not meant to limit the possible techniques one skilled in the art may use to prepare the compounds disclosed herein. Different methods to prepare the compounds of the present invention will be evident to those skilled in the art. Additionally, the various steps in the synthesis may be performed in an alternate sequence in order to give the desired compound or compounds. Examples of compounds of the present invention prepared by methods described in the general schemes are given in the preparations and examples section set out hereinafter. Preparation of homochiral examples may be carried out by techniques known to one skilled in the art. For example, homochiral compounds may be prepared by separation of racemic products by chiral phase preparative HPLC. Alternatively, the example compounds may be prepared by methods known to give enantiomerically enriched products.

The reactions and techniques described in this section are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art and alternate methods must then be used. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene et al. (*Protective Groups in Organic Synthesis*, Third Edition, Wiley and Sons (1999)).

Substituents used in the schemes do not necessarily correspond to those used in the claims.

Example compounds of the invention may be prepared using intermediate A, which may be prepared as described in WO 2014674661. Condensation of A with (2-aminophenyl)dimethyl phosphine oxide using a strong base such as lithium bis (trimethylsilyl)amide (LHMDS) provides intermediate B (X=CH). Palladium catalyzed cross-coupling with amines or primary carboxamides gives example compounds C (X=CH). Alternatively, A may be treated with intermediate D in the presence of a suitable base such as LHMDS to give B (X=N). Subsequent coupling with amines or amides in the presence of a catalytic source of palladium gives example compounds C (X=N). Intermediate D may be prepared by palladium catalyzed cross-coupling of 2-amino-3-iodopyridine with dimethyl phosphine oxide.

Scheme 1.

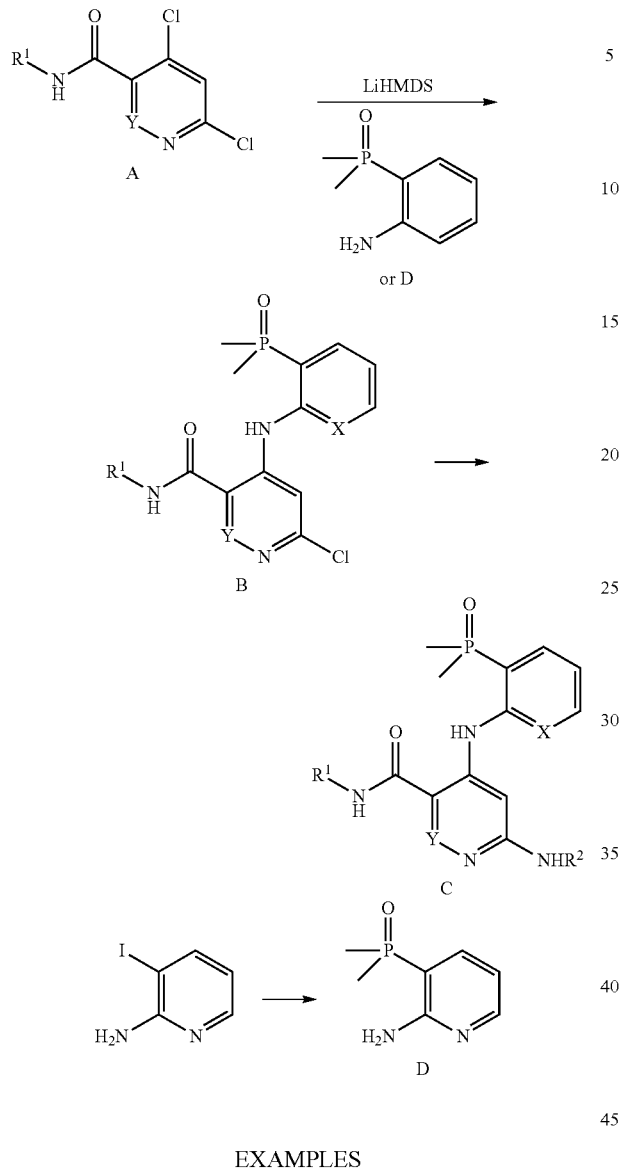

EXAMPLES

Preparation of compounds of Formula (I), and intermediates used in the preparation of compounds of Formula (I), can be prepared using procedures shown in the following Examples and related procedures. The methods and conditions used in these examples, and the actual compounds prepared in these Examples, are not meant to be limiting, but are meant to demonstrate how the compounds of Formula (I) can be prepared. Starting materials and reagents used in these examples, when not prepared by a procedure described herein, are generally either commercially available, or are reported in the chemical literature, or may be prepared by using procedures described in the chemical literature.

In the Examples given, the phrase "dried and concentrated" generally refers to drying of a solution in an organic solvent over either sodium sulfate or magnesium sulfate, followed by filtration and removal of the solvent from the filtrate (generally under reduced pressure and at a temperature suitable to the stability of the material being prepared). Column chromatography was performed with pre-packed silica gel cartridges using a medium pressure chromatography apparatus (Teledyne Corporation), eluting with the solvent or solvent mixture indicated. Preparative high performance liquid chromatography (HPLC) was performed using a reverse phase column (Waters Sunfire $C_{18}$, Waters Xbridge $C_{18}$, PHENOMENEX® Axia $C_{18}$, YMC S5 ODS or the like) of a size appropriate to the quantity of material being separated, generally eluting with a gradient of increasing concentration of methanol or acetonitrile in water, also containing 0.05% or 0.1% trifluoroacetic acid or 10 mM ammonium acetate, at a rate of elution suitable to the column size and separation to be achieved. Chemical names were determined using ChemDraw Ultra, version 9.0.5 (CambridgeSoft). The following abbreviations are used:

Preparative HPLC Method and Conditions:

The crude material was purified via preparative LC/MS with the following conditions: Column: XBridge C18, 19×200 mm, 5-µm particles; Mobile Phase A: 5:95 acetonitrile: water with 0.1% trifluoroacetic acid; Mobile Phase B: 95:5 acetonitrile: water with 0.1% trifluoroacetic acid; Gradient: 5-45% B over 20 minutes, then a 4-minute hold at 100% B; Flow: 20 mL/min. Fractions containing the desired product were combined and dried via centrifugal evaporation.

Analytical HPLC Method Conditions:

Analytical HPLC was performed on Shimadzu LC10AS liquid chromatographs: column, waters Acquity BEH C18, 1.7 µm 2.0×50 mm; gradient elution 0-100% gradient time 1.5 min and analysis time 2 min (solvent A, 90% water/10% MeOH/0.1% TFA; solvent B, 90% MeOH/10% water/0.1% TFA); flow rate, 1 mL/min; 220 nm as the detection wavelength.

Preparation 1

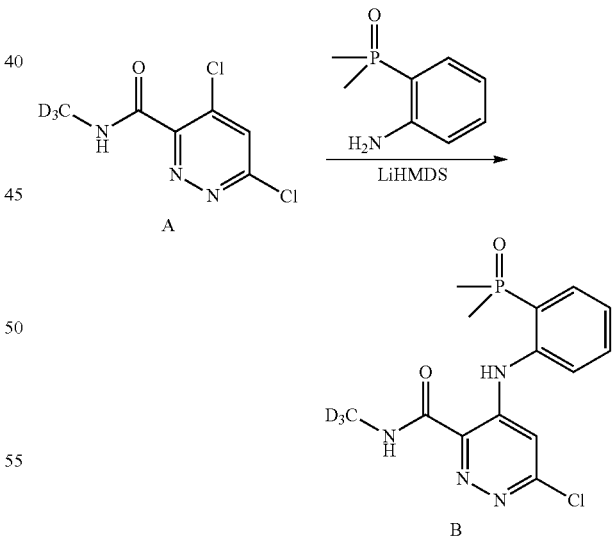

To a solution of (2-aminophenyl)dimethylphosphine oxide (0.5 g, 2.96 mmol) and A (0.606 g, 2.90 mmol; prepared as described in WO 2014/074661) in Tetrahydrofuran (10 mL) at rt was added lithium bis(trimethylsilyl) amide (7.24 ml, 7.24 mmol) over 5 min. The resulting mixture was stirred at rt for 1 h. The reaction was quenched with water (5 mL). The mixture was adjusted with 1 N HCl solution to pH 9-10, and further diluted with water (40 mL).

The precipitating product, B (0.65 g, 1.902 mmol, 65.6% yield) was collected and dried under vacuum. The material was used as it is for the next reaction. ¹H NMR (500 MHz, DMSO-d₆) δ 10.80-10.57 (m, 1H), 9.14 (br s, 1H), 7.92-7.84 (m, 1H), 7.74-7.67 (m, 1H), 7.62-7.55 (m, 1H), 7.51-7.45 (m, 1H), 1.68 (s, 3H), 1.66 (s, 3H). LC retention time 0.86 min. MS (E+) m/z: 342 (MH⁺).

Preparation of Example 1

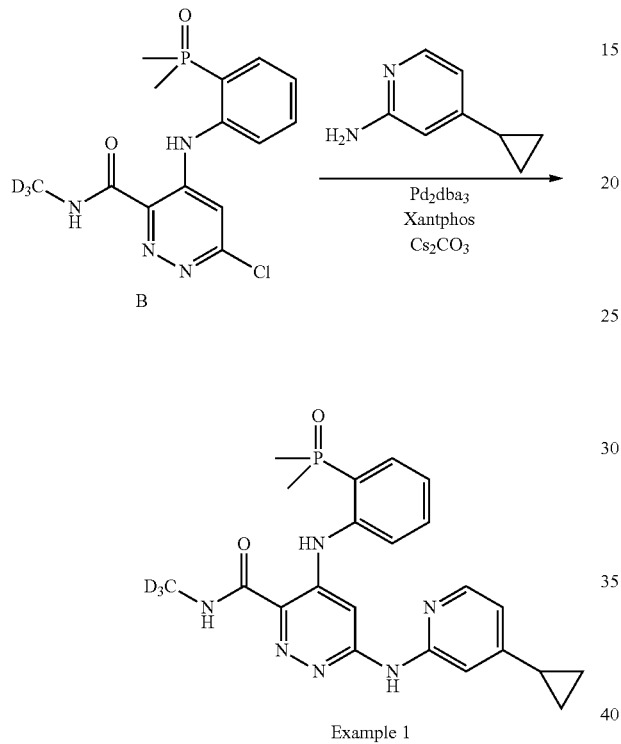

Example 1

To a solution of MY: A0F8C-061 (25 mg, 0.073 mmol) in dioxane (1.0 mL) was added 4-cyclopropylpyridin-2-amine (12.76 mg, 0.095 mmol), Pd₂(dba)₃ (6.70 mg, 7.32 µmol), Xantphos (8.47 mg, 0.015 mmol), Cs₂CO₃ (31.0 mg, 0.095 mmol) and was sparged with nitrogen for 5 min. The reaction was placed into a preheated 130° C. heating block for 2 h. The reaction mixture was diluted with DMSO, filtered and purified using preparative HPLC to give 11.5 mg of example 1 (36% yield). ¹H NMR (500 MHz, DMSO-d₆) δ 10.61-10.53 (m, 1H), 9.93-9.86 (m, 1H), 9.04 (s, 1H), 7.90-7.82 (m, 2H), 7.74-7.63 (m, 2H), 7.60-7.52 (m, 1H), 7.46-7.38 (m, 1H), 7.33-7.25 (m, 1H), 6.63-6.53 (m, 1H), 1.88-1.81 (m, 1H), 1.72 (s, 3H), 1.68 (s, 3H), 1.07-1.00 (m, 2H), 0.75-0.68 (m, 2H). LC retention time 0.88 min. MS (E+) m/z: 440 (MH⁺).

A procedure similar to that described in the synthesis of Example 1 was used to prepare the following examples shown in Table 1.

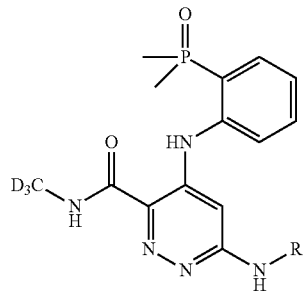

C

TABLE 1

Analytical HPLC and mass spectrometry results of series C.

| Example number | Series C: R | Rt (min) | m/z [M + H]⁺ |
|---|---|---|---|
| 2 | ![cyclopropyl ketone] | 0.86 | 391 |
| 3 | ![2,6-dimethylpyrimidin-4-yl] | 0.81 | 429 |
| 4 | ![6-methoxypyridazin-3-yl] | 0.83 | 431 |
| 5 | ![5-cyclopropylpyridin-2-yl] | 0.89 | 440 |
| 6 | ![6-(2-hydroxypropan-2-yl)pyridin-3-yl] | 0.84 | 458 |
| 7 | ![6-morpholinopyridin-3-yl] | 0.86 | 485 |

TABLE 1-continued

Analytical HPLC and mass spectrometry results of series C.

| Example number | Series C: R | Rt (min) | m/z [M + H]+ |
|---|---|---|---|
| 8 | 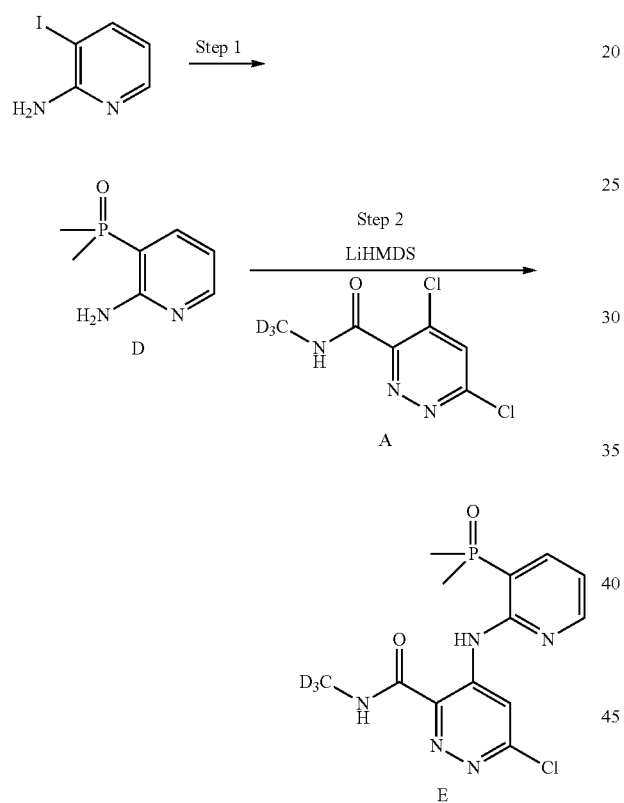 | 0.82 | 403 |

Preparation 2

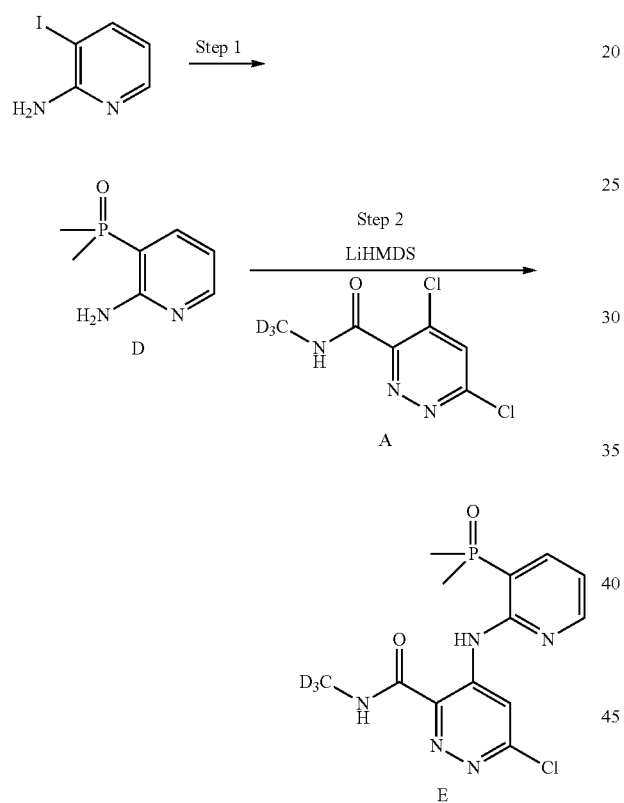

Step 1:

To a solution of 3-iodopyridin-2-amine (600 mg, 2.73 mmol), dimethylphosphine oxide (255 mg, 3.27 mmol) in 5 mL of 1,4-dioxane were added K$_3$PO$_4$ (637 mg, 3.00 mmol), diacetoxypalladium (61.2 mg, 0.273 mmol) and Xantphos (189 mg, 0.327 mmol), the mixture was purged with N$_2$ and stirred at 130° C. for 16, LC-MS indicated the desired product. The mixture was passed through an Isco column eluting with MeOH/DCM (0-15%, gradient time=20 min) to give compound D in 56% yield (260 mg, 1.528 mmol). $^1$H NMR (499 MHz, CHLOROFORM-d) δ 8.19 (dt, J=4.7, 2.1 Hz, 1H), 7.37 (ddd, J=13.8, 7.5, 1.8 Hz, 1H), 6.65 (ddd, J=7.3, 5.1, 1.9 Hz, 1H), 6.15 (br. s., 2H), 1.79 (s, 3H), 1.77 (s, 3H). LC retention time 0.13 min. MS (E+) m/z: 171.35 (MH+).

Step-2:

To a solution of 4,6-dichloro-N-trideuteromethyl-pyridazine-3-carboxamide (A, 307 mg, 1.469 mmol; prepared as described in WO 2014/074661) and (2-aminopyridin-3-yl)dimethylphosphine oxide (D, 250 mg, 1.469 mmol) in tetrahydrofuran (5 mL) at 0° C. was added lithium bis(trimethylsilyl)amide in THF (3.67 mL, 3.67 mmol) over 5 min. The resulting mixture was stirred at 0° C. for 2 h. The reaction was quenched with water (2 mL). The mixture was concentrated under vacuum and the residue was purified with isco column (24 g, MeOH/DCM=0-15%, gradient time=20 min) to give compound E (recovered the phosphine oxide). $^1$H NMR (400 MHz, DMSO-d$_6$) δ11.75 (s, 1H), 9.18 (s, 1H), 8.80 (s, 1H), 8.60-8.54 (m, 1H), 8.14 (ddd, J=13.1, 7.7, 1.9 Hz, 1H), 7.28 (dd, J=6.5, 4.8 Hz, 1H), 1.85 (s, 3H), 1.82 (s, 3H). LC retention time 0.83 min. MS (E+) m/z: 343 (MH+).

Preparation of Example 9

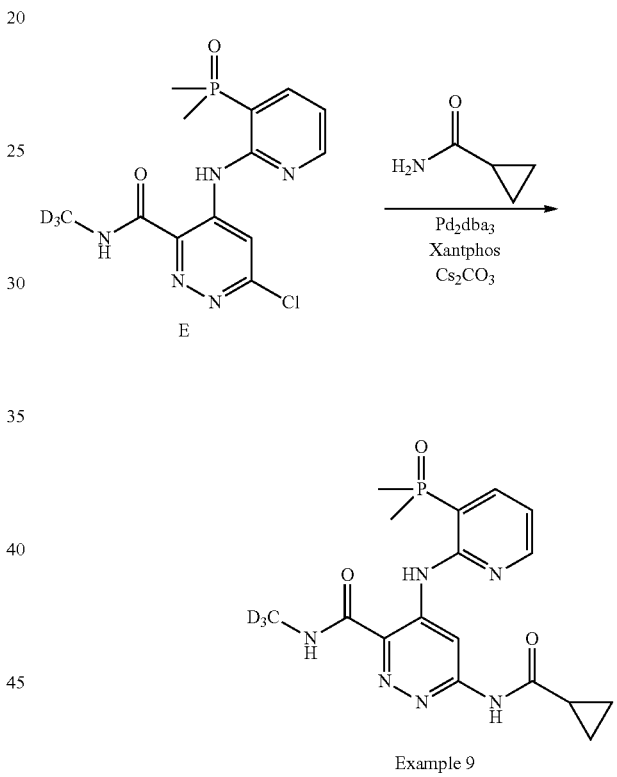

A mixture of E (15 mg, 0.044 mmol), cyclopropanecarboxamide (7.45 mg, 0.088 mmol), Xantphos (3.80 mg, 6.56 μmol), Pd$_2$(dba)$_3$ (3.01 mg, 3.28 μmop and Cs$_2$CO$_3$ (28.5 mg, 0.088 mmol) in dioxane (0.7 mL) was sparged with nitrogen for 2 min., and then it was stirred at 130° C. for 3 h. The crude product was diluted with DMSO and filtered, before being purified using preparative HPLC providing 5.5 mg (32% yield) of Example 9. $^1$H NMR (500 MHz, DMSO-d$_6$) δ 11.40-11.30 (m, 1H), 9.32-9.22 (m, 1H), 9.17-9.00 (m, 1H), 8.51-8.42 (m, 1H), 8.20-8.06 (m, 1H), 7.28-7.19 (m, 1H), 1.86-1.70 (m, 6H), 1.20-1.08 (m, 1H), 0.90-0.77 (m, 4H). LC retention time 0.77 min. MS (E+) m/z: 392 (MH+).

A procedure similar to that described in the synthesis of Example 9 was used to prepare the following examples as shown in Table 2:

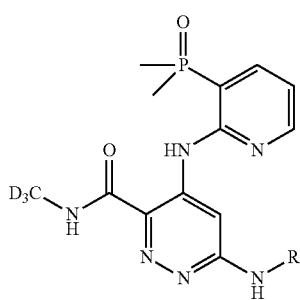

TABLE 2

Analytical HPLC and mass spectrometry results of series F.

| Example number | Series F: R | Rt (min) | m/z [M + H]⁺ |
|---|---|---|---|
| 10 | 6-methylpyrazin-2-yl | 0.81 | 416 |
| 11 | 5-tert-butylisoxazol-3-yl | 0.88 | 447 |
| 12 | 4-cyclopropylpyridin-2-yl | 0.84 | 441 |
| 13 | 5-(trifluoromethoxy)pyridin-2-yl | 0.88 | 485 |
| 14 | pyridin-2-yl | 0.78 | 401 |
| 15 | 5-fluoropyridin-2-yl | 0.86 | 419 |
| 16 | 5-(2-hydroxypropan-2-yl)pyridin-2-yl | 0.85 | 459 |
| 17 | 5-cyclopropylpyridin-2-yl | 0.88 | 441 |
| 18 | 6-methylpyridin-2-yl | 0.84 | 415 |
| 19 | ethyl ester | 0.85 | 396 |
| 20 | 4-(methoxymethyl)pyridin-2-yl | 0.83 | 445 |
| 21 | 4-methylpyridin-2-yl | 0.82 | 415 |
| 22 | 6-fluoropyridin-2-yl | 0.84 | 419 |
| 23 | 1-methyl-1H-pyrazol-3-yl | 0.81 | 404 |
| 24 | 6-methoxypyridin-2-yl | 0.85 | 431 |
| 25 | 4-fluoropyridin-2-yl | 0.82 | 419 |

TABLE 2-continued
Analytical HPLC and mass spectrometry results of series F.
| Example number | Series F: R | Rt (min) | m/z [M + H]+ |
|---|---|---|---|
| 26 | 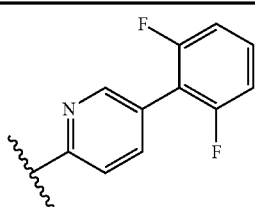 | 0.88 | 514 |
| 27 | 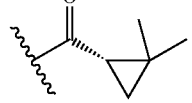 | 0.88 | 420 |
| 28 | 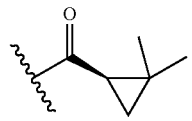 [SMILES: *C(=O)[C@@H]1CC1(C)C] | 0.96 | 420 |
| 29 | 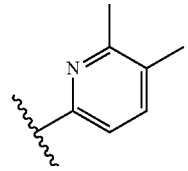 [SMILES: *c1ccc(C)c(C)n1] | 0.82 | 429 |
| 30 | 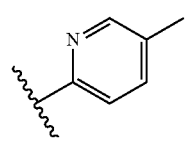 [SMILES: *c1ccc(C)cn1] | 0.81 | 415 |
| 31 | 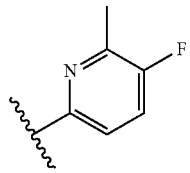 [SMILES: *c1ccc(F)c(C)n1] | 0.86 | 433 |
| 32 | 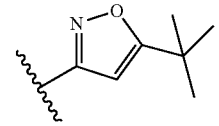 [SMILES: *c1cc(C(C)(C)C)on1] | 0.88 | 447 |
| 33 | 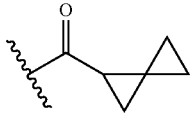 [SMILES: *C(=O)C1CC12CC2] | 0.85 | 418 |
| 34 | 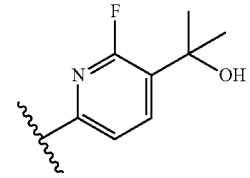 [SMILES: *c1ccc(C(C)(C)O)c(F)n1] | 0.82 | 477 |
| 35 | 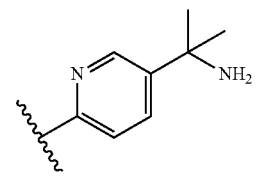 [SMILES: *c1ccc(C(C)(C)N)cn1] | 0.81 | 458 |
| 36 | 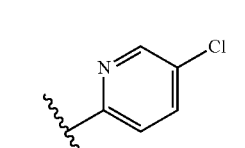 | 0.85 | 493 |
| 37 | 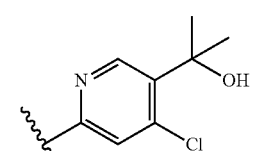 | 0.86 | 435 |
| 38 | 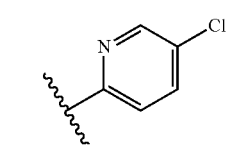 [SMILES: *c1ccc(Cl)cn1] | 0.84 | 446 |
| 39 | 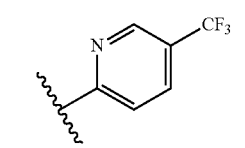 [SMILES: *c1ccc(C(F)(F)F)cn1] | 0.88 | 469 |
| 40 | 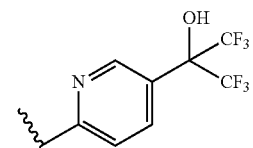 | 0.83 | 469 |
| 41 |  | 0.89 | 567 |

TABLE 2-continued

Analytical HPLC and mass spectrometry results of series F.

| Example number | Series F: R | Rt (min) | m/z [M + H]+ |
|---|---|---|---|
| 42 | 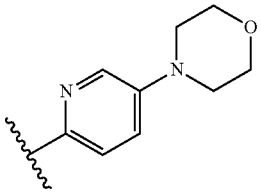 [SMILES: *c1ccc(N2CCOCC2)cn1] | 0.85 | 486 |
| 43 | 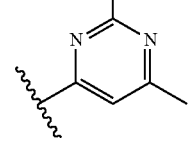 | 0.82 | 430 |

TABLE 3

$^1$H NMR data of examples 1-26.

| Compound | $^1$H NMR |
|---|---|
| 1 | $^1$H NMR (500 MHz, DMSO-d$_6$) δ 10.61-10.53 (m, 1H), 9.93-9.86 (m, 1H), 9.04 (s, 1H), 7.90-7.82 (m, 2H), 7.74-7.63 (m, 2H), 7.60-7.52 (m, 1H), 7.46-7.38 (m, 1H), 7.33-7.25 (m, 1H), 6.63-6.53 (m, 1H), 1.88-1.81 (m, 1H), 1.72 (s, 3H), 1.68 (s, 3H), 1.07-1.00 (m, 2H), 0.75-0.68 (m, 2H) |
| 2 | $^1$H NMR (500 MHz, DMSO-d$_6$) δ 10.64-10.55 (m, 1H), 9.04-8.96 (m, 1H), 7.85-7.76 (m, 1H), 7.73-7.65 (m, 1H), 7.62-7.56 (m, 1H), 7.48-7.35 (m, 2H), 1.95 (br d, J = 4.3 Hz, 1H), 1.65-1.61 (m, 3H), 1.61-1.57 (m, 3H), 0.79-0.66 (m, 4H) |
| 3 | $^1$H NMR (500 MHz, DMSO-d$_6$) δ 10.74-10.66 (m, 1H), 9.20-9.11 (m, 1H), 7.95-7.86 (m, 1H), 7.76-7.67 (m, 1H), 7.64-7.55 (m, 1H), 7.53-7.45 (m, 1H), 7.33-7.24 (m, 1H), 2.42-2.39 (m, 3H), 2.38-2.33 (m, 3H), 1.71-1.68 (m, 3H), 1.68-1.65 (m, 3H) |
| 4 | $^1$H NMR (500 MHz, DMSO-d$_6$) δ 10.71 (br s, 1H), 9.07 (br s, 1H), 7.83 (br dd, J = 12.2, 7.6 Hz, 1H), 7.79-7.71 (m, 1H), 7.70-7.58 (m, 1H), 7.58-7.50 (m, 1H), 7.42 (br t, J = 7.4 Hz, 2H), 7.30-7.16 (m, 2H), 7.16-7.06 (m, 1H), 7.00 (br s, 1H), 3.88 (s, 3H), 3.12 (s, 1H), 1.67 (s, 3H), 1.66 (s, 3H) |
| 5 | $^1$H NMR (500 MHz, DMSO-d$_6$) δ 10.56-10.50 (m, 1H), 9.94-9.88 (m, 1H), 9.02-8.95 (m, 1H), 7.88-7.79 (m, 2H), 7.69-7.62 (m, 2H), 7.56-7.50 (m, 1H), 7.45-7.35 (m, 2H), 7.31-7.24 (m, 1H), 1.85-1.78 (m, 1H), 1.65 (s, 3H), 1.63 (s, 3H), 0.88-0.83 (m, 2H), 0.60-0.55 (m, 2H) |
| 6 | $^1$H NMR (500 MHz, DMSO-d$_6$) δ 10.55-10.47 (m, 1H), 10.02-9.93 (m, 1H), 9.02-8.90 (m, 1H), 8.14-8.05 (m, 1H), 7.90-7.79 (m, 1H), 7.73-7.60 (m, 3H), 7.58-7.52 (m, 1H), 7.46-7.37 (m, 2H), 1.68 (s, 3H), 1.64 (s, 3H), 1.41 (s, 6H) |
| 7 | $^1$H NMR (500 MHz, DMSO-d$_6$) δ 10.89-10.81 (m, 1H), 9.12-9.03 (m, 1H), 7.93-7.88 (m, 1H), 7.87-7.78 (m, 1H), 7.73-7.66 (m, 1H), 7.59-7.45 (m, 3H), 3.74 (br, 4H), 3.08-3.02 (m, 4H), 1.70 (s, 3H), 1.67 (s, 3H) |
| 8 | $^1$H NMR (500 MHz, DMSO-d$_6$) δ 10.44 (br s, 1H), 9.64-9.60 (m, 1H), 8.92 (br s, 1H), 7.86-7.79 (m, 1H), 7.67-7.61 (m, 1H), 7.54-7.48 (m, 1H), 7.47-7.43 (m, 1H), 7.41-7.35 (m, 1H), 7.20-7.15 (m, 1H), 6.09-6.03 (m, 1H), 3.61 (br 3H), 1.65-1.63 (m, 3H), 1.61 (s, 3H) |
| 9 | $^1$H NMR (500 MHz, DMSO-d$_6$) δ 11.40-11.30 (m, 1H), 9.32-9.22 (m, 1H), 9.17-9.00 (m, 1H), 8.51-8.42 (m, 1H), 8.20-8.06 (m, 1H), 7.28-7.19 (m, 1H), 1.86-1.70 (m, 6H), 1.20-1.08 (m, 1H), 0.90-0.77 (m, 4H) |
| 10 | $^1$H NMR (500 MHz, DMSO-d$_6$) δ 11.59-11.52 (m, 1H), 10.56-10.50 (m, 1H), 9.46-9.39 (m, 1H), 9.13-9.06 (m, 1H), 8.73-8.66 (m, 1H), 8.59-8.52 (m, 1H), 8.20-8.10 (m, 1H), 8.08-8.03 (m, 1H), 7.29-7.22 (m, 1H), 2.43-2.37 (m, 3H), 1.89-1.82 (m, 6H) |
| 11 | $^1$H NMR (500 MHz, DMSO-d$_6$) δ 8.54-8.42 (m, 1H), 8.08-7.97 (m, 1H), 7.24-7.09 (m, 1H), 4.20-4.10 (m, 1H), 3.93-3.84 (m, 1H), 3.65-3.53 (m, 2H), 3.19-3.12 (m, 1H), 1.87-1.78 (m, 6H), 1.75-1.68 (m, 3H), 1.22-1.15 (m, 6H) |
| 12 | $^1$H NMR (500 MHz, DMSO-d$_6$) δ 11.44 (s, 1H), 9.99 (br s, 1H), 9.30-9.22 (m, 1H), 9.03 (br s, 1H), 8.54-8.44 (m, 1H), 8.17-8.01 (m, 2H), 7.36 (s, 1H), 7.22 (dd, J = 7.2, 5.0 Hz, 1H), 6.65 (br d, J = 4.3 Hz, 1H), 1.84 (d, J = 13.4 Hz, 6H), 1.79-1.65 (m, 1H), 1.06 (br dd, J = 8.2, 2.1 Hz, 2H), 0.75 (dd, J = 4.7, 2.0 Hz, 2H) |
| 13 | $^1$H NMR (500 MHz, DMSO-d$_6$) δ 11.53 (s, 1H), 10.47 (s, 1H), 9.26 (s, 1H), 9.09 (s, 1H), 8.67-8.51 (m, 1H), 8.35 (br s, 1H), 8.19-8.05 (m, 1H), 7.83 (br d, J = 4.6 Hz, 2H), 7.24 (dd, J = 7.0, 5.2 Hz, 1H), 1.85 (d, J = 13.4 Hz, 6H) |
| 14 | $^1$H NMR (500 MHz, DMSO-d$_6$) δ 11.49 (s, 1H), 10.19 (s, 1H), 9.34 (s, 1H), 9.06 (s, 1H), 8.61-8.47 (m, 1H), 8.26 (br d, J = 4.0 Hz, 1H), 8.18-8.05 (m, 1H), 7.79-7.69 (m, 1H), 7.62 (d, J = 8.2 Hz, 1H), 7.23 (dd, J = 7.3, 4.9 Hz, 1H), 7.02-6.88 (m, 1H), 1.85 (d, J = 13.4 Hz, 6H) |

TABLE 3-continued

¹H NMR data of examples 1-26.

| Compound | ¹H NMR |
|---|---|
| 15 | ¹H NMR (500 MHz, DMSO-d$_6$) δ 11.50 (s, 1H), 10.28 (br s, 1H), 9.22 (s, 1H), 9.08 (br s, 1H), 8.61-8.49 (m, 1H), 8.26 (br s, 1H), 8.13 (br dd, J = 12.8, 7.7 Hz, 1H), 7.72 (br d, J = 2.8 Hz, 2H), 7.33-7.13 (m, 1H), 1.85 (br d, J = 13.4 Hz, 6H) |
| 16 | ¹H NMR (500 MHz, DMSO-d$_6$) δ 11.49 (s, 1H), 10.14 (s, 1H), 9.27 (s, 1H), 9.07 (s, 1H), 8.60-8.46 (m, 1H), 8.34 (d, J = 1.8 Hz, 1H), 8.21-8.07 (m, 1H), 7.79 (dd, J = 8.7, 2.3 Hz, 1H), 7.62 (d, J = 8.9 Hz, 1H), 7.24 (dd, J = 7.3, 5.2 Hz, 1H), 5.11 (s, 1H), 1.85 (d, J = 13.4 Hz, 6H), 1.45 (s, 6H) |
| 17 | ¹H NMR (500 MHz, DMSO-d$_6$) δ 11.53-11.43 (m, 1H), 10.08 (s, 1H), 9.25 (s, 1H), 9.05 (s, 1H), 8.60-8.49 (m, 1H), 8.21-8.06 (m, 2H), 7.56 (d, J = 8.9 Hz, 1H), 7.38 (dd, J = 8.7, 2.3 Hz, 1H), 7.23 (dd, J = 7.3, 4.9 Hz, 1H), 1.85 (d, J = 13.4 Hz, 6H), 0.96-0.90 (m, 2H), 0.67 (br d, J = 5.8 Hz, 2H) |
| 18 | ¹H NMR (500 MHz, DMSO-d$_6$) δ 11.54-11.42 (m, 1H), 10.17 (br s, 1H), 9.48 (br s, 1H), 9.06 (br s, 1H), 8.63-8.44 (m, 1H), 8.14 (br dd, J = 12.8, 7.6 Hz, 1H), 7.59 (t, J = 7.8 Hz, 1H), 7.37-7.14 (m, 2H), 6.81 (d, J = 7.3 Hz, 1H), 2.36 (s, 3H), 1.85 (br d, J = 13.4 Hz, 6H) |
| 19 | ¹H NMR (500 MHz, DMSO-d$_6$) δ 11.52 (s, 1H), 9.10 (s, 1H), 9.05 (s, 1H), 8.53-8.48 (m, 1H), 8.13 (br dd, J = 13.0, 7.5 Hz, 1H), 7.24 (dd, J = 7.3, 5.2 Hz, 1H), 4.16 (q, J = 7.0 Hz, 2H), 1.83 (d, J = 13.4 Hz, 6H), 1.24 (t, J = 7.0 Hz, 3H) |
| 20 | ¹H NMR (500 MHz, DMSO-d$_6$) δ 11.51 (br s, 1H), 10.22 (br s, 1H), 9.25 (br s, 1H), 9.12 (br s, 1H), 8.61-8.49 (m, 1H), 8.28-8.06 (m, 2H), 7.70 (br s, 1H), 7.23 (dd, J = 7.4, 5.0 Hz, 1H), 6.88 (d, J = 5.0 Hz, 1H), 4.44 (s, 2H), 3.65 (s, 3H), 1.85 (d, J = 13.5 Hz, 6H) |
| 21 | ¹H NMR (500 MHz, DMSO-d$_6$) δ 11.59-11.31 (m, 1H), 10.13 (br s, 1H), 9.27 (br s, 1H), 9.11 (br s, 1H), 8.63-8.42 (m, 1H), 8.23-8.07 (m, 2H), 7.66-7.44 (m, 1H), 7.23 (dd, J = 7.3, 5.0 Hz, 1H), 6.81 (d, J = 4.9 Hz, 1H), 2.29 (s, 3H), 1.85 (d, J = 13.5 Hz, 6H) |
| 22 | ¹H NMR (500 MHz, DMSO-d$_6$) δ 11.59-11.42 (m, 1H), 10.46 (br s, 1H), 9.38 (s, 1H), 9.05 (br s, 1H), 8.60-8.39 (m, 1H), 8.11 (br dd, J = 13.1, 7.6 Hz, 1H), 7.87 (br d, J = 8.2 Hz, 1H), 7.47 (br d, J = 8.0 Hz, 1H), 7.25 (dd, J = 7.3, 5.0 Hz, 1H), 6.65 (br d, J = 6.5 Hz, 1H), 1.84 (d, J = 13.4 Hz, 6H) |
| 23 | ¹H NMR (500 MHz, DMSO-d$_6$) δ 11.45 (s, 1H), 9.79 (s, 1H), 9.00 (s, 1H), 8.85 (s, 1H), 8.58-8.43 (m, 1H), 8.13 (br dd, J = 12.2, 8.2 Hz, 1H), 7.56 (d, J = 1.5 Hz, 1H), 7.22 (dd, J = 7.3, 4.9 Hz, 1H), 6.25 (s, 1H), 2.65 (s, 3H), 1.84 (d, J = 13.4 Hz, 6H) |
| 24 | ¹H NMR (500 MHz, DMSO-d$_6$) δ 11.39 (br s, 1H), 10.21 (br s, 1H), 9.12-8.95 (m, 2H), 8.59-8.43 (m, 1H), 8.13 (br dd, J = 12.8, 7.9 Hz, 1H), 7.61 (t, J = 7.9 Hz, 1H), 7.24 (dd, J = 7.0, 5.1 Hz, 1H), 7.06 (br d, J = 7.7 Hz, 1H), 6.34 (d, J = 7.9 Hz, 1H), 3.65 (s, 3H), 1.82 (d, J = 13.5 Hz, 6H) |
| 25 | ¹H NMR (500 MHz, DMSO-d$_6$) δ 11.55-11.47 (m, 1H), 10.39 (s, 1H), 9.20-9.13 (m, 1H), 9.11-9.06 (m, 1H), 8.58-8.51 (m, 1H), 8.33-8.27 (m, 1H), 8.17-8.09 (m, 1H), 7.68-7.61 (m, 1H), 7.28-7.18 (m, 1H), 6.93-6.82 (m, 1H), 1.91-1.76 (m, 6H) |
| 26 | ¹H NMR (500 MHz, DMSO-d$_6$) δ 11.58-11.51 (m, 1H), 9.16-9.08 (m, 2H), 8.52-8.45 (m, 1H), 8.26-8.20 (m, 1H), 8.17-8.09 (m, 1H), 7.88-7.81 (m, 1H), 7.65-7.57 (m, 1H), 7.35-7.20 (m, 4H), 1.92-1.80 (m, 6H) |
| 27 | 1H NMR (500 MHz, DMSO-d6) δ 11.58-11.46 (m, 1H), 11.22-11.09 (m, 1H), 9.34-9.19 (m, 1H), 9.13-9.00 (m, 1H), 8.51-8.44 (m, 1H), 8.17-8.08 (m, 1H), 7.28-7.21 (m, 1H), 2.00-1.94 (m, 1H), 1.86-1.79 (m, 5H), 1.26-1.21 (m, 3H), 1.18-1.15 (m, 3H), 1.14-1.10 (m, 3H), 0.88-0.82 (m, 1H) |
| 28 | 1H NMR (500 MHz, DMSO-d6) δ 11.17 (br s, 1H), 9.30-9.24 (m, 1H), 9.09 (br s, 1H), 8.49-8.45 (m, 1H), 8.17-8.09 (m, 1H), 7.27-7.20 (m, 1H), 2.01-1.96 (m, 1H), 1.85-1.80 (m, 7H), 1.18-1.16 (m, 3H), 1.15-1.12 (m, 3H), 1.03-1.00 (m, 1H), 0.87-0.83 (m, 1H) |
| 29 | 1H NMR (500 MHz, DMSO-d6) δ 11.51-11.47 (m, 1H), 10.07-10.03 (m, 1H), 9.43-9.41 (m, 1H), 9.07-9.04 (m, 1H), 8.55-8.52 (m, 1H), 8.19-8.13 (m, 1H), 7.47-7.43 (m, 1H), 7.30-7.27 (m, 1H), 7.26-7.22 (m, 1H), 2.36-2.32 (m, 3H), 2.21-2.17 (m, 3H), 1.88-1.83 (m, 6H) |
| 30 | 1H NMR (500 MHz, DMSO-d6) δ 11.50-11.45 (m, 1H), 10.10-10.07 (m, 1H), 9.30-9.27 (m, 1H), 9.08-9.03 (m, 1H), 8.55-8.51 (m, 1H), 8.17-8.08 (m, 2H), 7.58-7.53 (m, 2H), 7.26-7.20 (m, 1H), 2.23 (s, 3H), 1.85 (d, J = 13.4 Hz, 6H) |
| 31 | 1H NMR (500 MHz, DMSO-d6) δ 11.49-11.46 (m, 1H), 10.22-10.18 (m, 1H), 9.35-9.31 (m, 1H), 9.03-9.00 (m, 1H), 8.56-8.52 (m, 1H), 8.17-8.11 (m, 1H), 7.60-7.54 (m, 1H), 7.42-7.38 (m, 1H), 7.26-7.22 (m, 1H), 2.35 (d, J = 1.8 Hz, 3H), 1.84 (br d, J = 13.4 Hz, 6H) |

TABLE 3-continued

¹H NMR data of examples 1-26.

| Compound | ¹H NMR |
|---|---|
| 32 | 1H NMR (500 MHz, DMSO-d6) δ 9.18-9.10 (m, 1H), 8.50-8.43 (m, 1H), 8.06-7.98 (m, 1H), 7.19-7.10 (m, 1H), 4.18-4.13 (m, 1H), 3.91-3.86 (m, 1H), 3.62-3.56 (m, 2H), 3.19-3.14 (m, 1H), 1.86-1.77 (m, 5H), 1.74-1.69 (m, 3H), 1.20-1.17 (m, 6H) |
| 33 | 1H NMR (500 MHz, DMSO-d6) δ 11.53 (s, 1H), 11.14 (s, 1H), 9.28 (s, 1H), 9.08 (s, 1H), 8.51-8.48 (m, 1H), 8.14 (br dd, J = 12.1, 6.9 Hz, 1H), 7.24 (dd, J = 7.2, 5.0 Hz, 1H), 2.45 (br d, J = 2.7 Hz, 1H), 1.82 (br d, J = 13.4 Hz, 6H), 1.42 (br s, 1H), 1.37 (br dd, J = 7.0, 3.1 Hz, 1H), 0.94-0.84 (m, 3H), 0.79-0.74 (m, 1H) |
| 34 | 1H NMR (500 MHz, DMSO-d6) δ 11.55 (s, 1H), 10.39 (s, 1H), 9.32 (s, 1H), 9.10 (s, 1H), 8.55-8.50 (m, 1H), 8.20-8.10 (m, 1H), 8.01 (br dd, J = 10.8, 8.4 Hz, 1H), 7.57 (br d, J = 8.2 Hz, 1H), 7.30-7.20 (m, 1H), 1.88-1.83 (m, 6H), 1.48 (s, 3H), 1.24 (s, 3H) |
| 35 | 1H NMR (500 MHz, DMSO-d6) δ 11.49 (s, 1H), 10.14 (s, 1H), 9.30 (s, 1H), 9.06 (s, 1H), 8.55 (br d, J = 3.1 Hz, 1H), 8.40 (br d, J = 1.8 Hz, 1H), 8.15 (br dd, J = 11.6, 7.6 Hz, 1H), 7.87 (br dd, J = 8.5, 2.4 Hz, 1H), 7.60 (br d, J = 8.9 Hz, 1H), 7.24 (br dd, J = 7.3, 4.9 Hz, 1H), 1.86 (br d, J = 4.0 Hz, 6H), 1.23 (s, 6H) |
| 36 | 1H NMR (500 MHz, DMSO-d6) δ 11.50 (s, 1H), 10.36-10.24 (m, 1H), 9.18-9.10 (m, 1H), 9.02 (s, 1H), 8.57-8.48 (m, 2H), 8.13 (br d, J = 12.5, 7.0 Hz, 1H), 8.00 (s, 1H), 7.25 (br dd, J = 7.3, 4.9 Hz, 1H), 1.85 (d, J = 13.4 Hz, 6H), 1.59 (s, 6H) |
| 37 | 1H NMR (500 MHz, DMSO-d6) δ 11.52 (s, 1H), 10.38 (s, 1H), 9.25 (s, 1H), 9.08 (s, 1H), 8.59-8.48 (m, 1H), 8.30 (d, J = 2.4 Hz, 1H), 8.14 (ddd, J = 13.0, 7.6, 1.4 Hz, 1H), 7.84 (dd, J = 9.0, 2.6 Hz, 1H), 7.73 (d, J = 8.9 Hz, 1H), 7.23 (dd, J = 7.3, 4.9 Hz, 1H), 1.85 (d, J = 13.4 Hz, 6H) |
| 38 | 1H NMR (500 MHz, DMSO-d6) δ 11.51 (s, 1H), 10.33 (s, 1H), 9.12-9.01 (m, 2H), 8.48 (br d, J = 2.4 Hz, 1H), 8.13 (br d, J = 7.6 Hz, 1H), 7.95 (br d, J = 9.8 Hz, 1H), 7.27-7.17 (m, 2H), 3.42 (br s, 2H), 1.91-1.80 (m, 6H), 1.37 (t, J = 7.0 Hz, 3H) |
| 39 | 1H NMR (500 MHz, DMSO-d6) δ 11.55 (s, 1H), 10.70 (s, 1H), 9.33 (s, 1H), 9.11 (s, 1H), 8.71-8.46 (m, 2H), 8.22-8.00 (m, 2H), 7.87 (br d, J = 8.5 Hz, 1H), 7.38-7.09 (m, 1H), 1.85 (br d, J = 13.4 Hz, 6H) |
| 40 | 1H NMR (500 MHz, DMSO-d6) δ 11.50 (s, 1H), 10.65 (s, 1H), 9.20 (s, 1H), 9.08 (s, 1H), 8.45 (br s, 1H), 8.14 (br dd, J = 12.7, 7.5 Hz, 1H), 8.02-7.89 (m, 1H), 7.84 (br d, J = 8.2 Hz, 1H), 7.40 (d, J = 7.3 Hz, 1H), 7.25 (br dd, J = 7.2, 5.0 Hz, 1H), 1.84 (d, J = 13.4 Hz, 6H) |
| 41 | 1H NMR (500 MHz, DMSO-d6) δ 11.51 (s, 1H), 10.55-10.35 (m, 1H), 9.26 (s, 1H), 9.07 (s, 1H), 8.50 (br d, J = 14.3 Hz, 2H), 8.13 (br dd, J = 13.1, 7.6 Hz, 1H), 7.96 (br d, J = 9.2 Hz, 1H), 7.81 (br d, J = 8.9 Hz, 1H), 7.33-7.18 (m, 1H), 1.85 (br d, J = 13.4 Hz, 6H) |
| 42 | 1H NMR (500 MHz, DMSO-d6) δ 11.62 (br s, 1H), 9.03 (br s, 2H), 8.58-8.54 (m, 1H), 8.15 (br dd, 3 = 12.1, 7.8 Hz, 1H), 7.99 (br s, 1H), 7.57 (br d, J = 7.9 Hz, 1H), 7.46 (br d, J = 8.2 Hz, 1H), 7.16 (s, 1H), 7.06 (s, 1H), 3.81-3.72 (m, 4H), 3.12 (br s, 4H), 1.85 (d, J = 13.4 Hz, 6H) |
| 43 | 1H NMR (500 MHz, DMSO-d6) δ 11.56 (s, 1H), 10.55 (br s, 1H), 9.44 (s, 1H), 9.13 (br s, 1H), 8.57-8.54 (m, 1H), 8.18-8.12 (m, 1H), 7.29-7.24 (m, 2H), 2.45 (s, 3H), 2.33 (s, 3H), 1.86 (s, 3H), 1.83 (s, 3H) |

BIOLOGICAL ASSAYS

Probe Displacement Assay (HTRF Format)

To 10 μL 26 nM fluorescein labeled probe plus 0.2 nM anti-6×His-terbium labeled antibody (Medarex, labeled by Cisbio) in assay buffer (20 mM Hepes pH 7.5, 150 mM NaCl, 10 mM MgCl2, 2 mM DTT, 50 μg/mL BSA, and 0.015% Brij 35) was added 10 μL recombinant human His-tagged Tyk2 pseudokinase domain (His-TVMV-Tyk2, 575-869) to a final concentration of 0.5 nM. After 1 h at room temperature, the HTRF signal (ratio of fluorescence intensities at emission wavelengths for fluorescein acceptor at 520 nm and terbium donor at 495 nm) was measured on an Envision Plate Reader. Percent inhibition was calculated by comparison to a control without inhibitor and a control without protein. Dose response curves were generated to determine the concentration required for inhibiting 50% of the HTRF signal (EC50).

Protein Sequence of recombinant His-tagged Tyk2 (575-869):

(SEQ ID NO: 1)

MGSSHHHHHH SSGETVRFQG HMNLSQLSFH RVDQKEITQL

SHLGQGTRTN VYEGRLRVEG SGDPEEGKMDDEDPLVPGRD

RGQELRVVLK VLDPSHHDIA LAFYETASLM SQVSHTHLAF

VHGVCVRGPE NIMVTEYVEHGPLDVWLRRE RGHVPMAWKM

VVAQQLASAL SYLENKNLVH GNVCGRNILL ARLGLAEGTS

PFIKLSDPGVGLGALSREER VERIPWLAPE CLPGGANSLS

TAMDKWGFGA TLLEICFDGE APLQSRSPSE

KEHFYQRQHRLPEPSCPQLA TLTSQCLTYE PTQRPSFRTI

LRDLTRL.

| Binding Data | |
|---|---|
| Example No. | Binding IC$_{50}$ (uM) |
| 1 | 3.4E-03 |
| 2 | 7.4E-03 |
| 3 | 1.6E-03 |
| 4 | 1.0E-02 |
| 5 | 5.2E-03 |
| 6 | 2.2E-03 |
| 7 | 1.3E-02 |
| 8 | 1.2E-02 |
| 9 | 1.4E-03 |
| 11 | 6.2E-04 |
| 12 | 7.4E-04 |
| 13 | 4.3E-04 |
| 14 | 7.9E-04 |
| 15 | 5.4E-04 |
| 16 | 2.9E-04 |
| 17 | 2.7E-04 |
| 18 | 4.4E-04 |
| 19 | 9.8E-03 |
| 20 | 5.8E-04 |
| 21 | 6.2E-04 |
| 22 | 3.7E-05 |
| 23 | 2.0E-03 |
| 24 | 9.7E-04 |
| 25 | 5.8E-04 |
| 26 | 4.8E-04 |
| 27 | 1.3E-02 |
| 28 | 1.7E-02 |
| 29 | 5.4E-04 |
| 30 | 5.6E-04 |
| 31 | 5.4E-04 |
| 32 | 6.0E-01 |
| 33 | 2.9E-03 |
| 34 | 8.6E-04 |
| 35 | 1.2E-03 |
| 36 | 5.3E-04 |
| 37 | 3.8E-04 |
| 38 | NT |
| 39 | 3.4E-04 |
| 40 | 4.6E-04 |
| 41 | 9.2E-04 |
| 42 | 6.2E-04 |
| 43 | NT |

Kit225 T Cell Assay

Kit225 T cells with a stably-integrated STAT-dependent luciferase reporter were plated in RPMI (Gibco) containing 10% heat-inactivated FBS (Gibco) and 100 U/mL PenStrep (Gibco). The cells were then stimulated with either 20 ng/mL human recombinant IL-23 or 200 U/mL human recombinant IFNα (PBL InterferonSource) for 5-6 hours. Luciferase expression was measured using the STEADY-GLO® Luciferase Assay System (Promega) according to the manufacturer's instructions. Inhibition data were calculated by comparison to no inhibitor control wells for 0% inhibition and non-stimulated control wells for 100% inhibition. Dose response curves were generated to determine the concentration required to inhibit 50% of cellular response (IC$_{50}$) as derived by non-linear regression analysis.

| Kit225 T Cell Inhibition Data | | |
|---|---|---|
| Example No. | IL23 Kit 225 IC$_{50}$ (uM) | IFN Kit 225 IC$_{50}$ (uM) |
| 1 | 0.383 | 0.242 |
| 2 | 1.805 | 3.171 |
| 3 | 3.473 | 1.560 |
| 4 | 2.568 | 9.157 |
| 5 | 0.390 | 0.337 |
| 6 | 3.113 | 0.423 |
| 7 | 1.436 | 0.799 |
| 8 | 3.704 | 1.765 |
| 9 | 0.282 | 0.514 |
| 11 | 0.298 | 0.266 |
| 12 | 0.092 | 0.144 |
| 13 | 0.044 | 0.022 |
| 14 | 0.212 | 0.125 |
| 15 | 0.114 | 0.048 |
| 16 | 1.206 | 0.673 |
| 17 | 0.058 | 0.043 |
| 18 | 0.058 | 0.033 |
| 19 | 0.817 | 4.156 |
| 20 | 0.067 | 0.050 |
| 21 | 0.019 | 0.050 |
| 22 | 0.040 | 0.015 |
| 23 | 1.152 | 0.666 |
| 24 | 0.084 | 0.033 |
| 25 | 0.132 | 0.090 |
| 26 | 0.428 | 0.402 |
| 27 | 12.5 | 4.61 |
| 28 | 6.32 | 6.34 |
| 29 | 0.0620 | 0.0228 |
| 30 | 0.121 | 0.0323 |
| 31 | 0.0453 | 0.0539 |
| 32 | 12.5 | 12.5 |
| 33 | 3.72 | 1.48 |
| 34 | 1.35 | 0.350 |
| 35 | 1.77 | 2.29 |
| 36 | 0.927 | 0.905 |
| 37 | 0.0528 | 0.0740 |
| 38 | NT | NT |
| 39 | 0.0594 | 0.217 |
| 40 | 0.256 | 0.137 |
| 41 | 0.322 | 0.206 |
| 42 | 0.298 | 0.266 |
| 43 | NT | NT |

What is claimed is:

1. A compound having the following formula I:

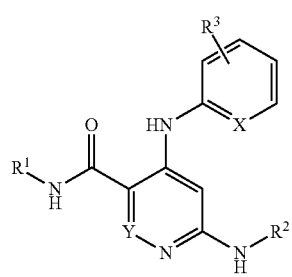

wherein:

X is —N— or —CH—;

Y is —N— or —CH—;

$R^1$ is $CD_3$, $C_{1-3}$ alkyl or $C_{3-6}$ cycloalkyl;

$R^2$ is CO—$C_{3-6}$ cycloalkyl, $C_{5-8}$ aryl or a 5-7 membered heterocyclyl having carbon atoms and 1-4 heteroatoms independently selected from N, O, and S, substituted with 0-4 $R^{2a}$;

$R^{2a}$ is independently, at each occurrence, hydrogen, halogen, $C_{1-6}$ alkyl, $C_{1-6}$ alkoxy, $C_{3-6}$ cycloalkyl, halo $C_{1-6}$ alkyl, hydroxy $C_{1-6}$ alkyl, $C_{5-8}$ aryl or a 5-7 membered heterocyclyl having carbon atoms and 1-4 heteroatoms independently selected from N, O, and S, said aryl or heterocyclyl substituted with 0-2 $R^a$;

$R^a$ is hydrogen, halogen or $C_{1-4}$ alkyl;

$R^3$ is P(O)—($C_{1-4}$ alkyl)$_2$;

or a pharmaceutically-acceptable salt thereof.

2. The compound according to claim 1, of the formula

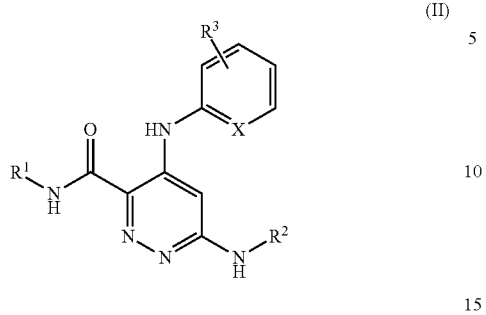
(II)

wherein:

X is —N— or —CH—;

$R^1$ is $CD_3$, $C_{1-3}$ alkyl or $C_{3-6}$ cycloalkyl;

$R^2$ is CO—$C_{3-6}$ cycloalkyl, $C_{5-8}$ aryl or a 5-7 heterocyclyl having carbon atoms and 1-4 heteroatoms independently selected from N, O, and S, substituted with 0-4 $R^{2a}$;

$R^{2a}$ is independently, at each occurrence, hydrogen, halogen, $C_{1-6}$ alkyl, $C_{1-6}$ alkoxy, $C_{3-6}$ cycloalkyl, halo $C_{1-6}$ alkyl, hydroxy $C_{1-6}$ alkyl, $C_{5-8}$ aryl or a 5-7 membered heterocyclyl having carbon atoms and 1-4 heteroatoms independently selected from N, O, and S, said aryl or heterocyclyl substituted with 0-2 $R^a$;

$R^a$ is hydrogen, halogen or $C_{1-4}$ alkyl;

$R^3$ is P(O)—$(C_{1-4}$ alkyl$)_2$;

or a pharmaceutically-acceptable salt thereof.

3. The compound according to claim 2, of the formula

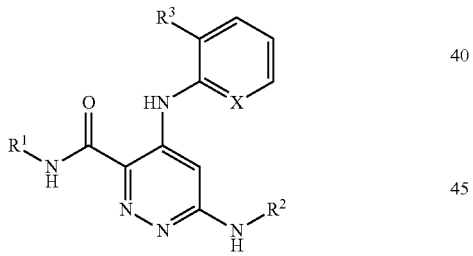

wherein:

X is —N— or —CH—;

$R^1$ is $CD_3$, $C_{1-3}$ alkyl or $C_{3-6}$ cycloalkyl;

$R^2$ is CO—$C_{3-6}$ cycloalkyl, $C_{5-8}$ aryl or a 5-7 membered heterocyclyl having carbon atoms and 1-4 heteroatoms independently selected from N, O, and S, substituted with 0-4 $R^{2a}$;

$R^{2a}$ is independently, at each occurrence, hydrogen, halogen, $C_{1-6}$ alkyl, $C_{1-6}$ alkoxy, $C_{3-6}$ cycloalkyl, halo $C_{1-6}$ alkyl, hydroxy $C_{1-6}$ alkyl, $C_{5-8}$ aryl or a 5-7 membered heterocyclyl having carbon atoms and 1-4 heteroatoms independently selected from N, O, and S, said aryl or heterocyclyl substituted with 0-2 $R^a$;

$R^a$ is hydrogen, halogen or $C_{1-4}$ alkyl;

$R^3$ is P(O)—$(C_{1-4}$ alkyl$)_2$;

or a pharmaceutically-acceptable salt thereof.

4. The compound according to claim 3, of the formula

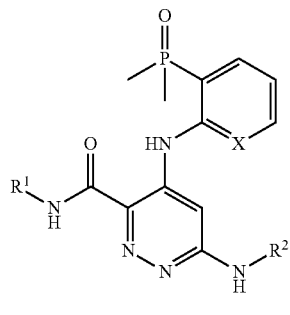

wherein:

X is —N— or —CH—;

$R^1$ is $CD_3$, $C_{1-3}$ alkyl or $C_{3-6}$ cycloalkyl;

$R^2$ is CO—$C_{3-6}$ cycloalkyl, $C_{5-8}$ aryl or a 5-7 membered heterocyclyl having carbon atoms and 1-4 heteroatoms independently selected from N, O, and S, substituted with 0-4 $R^{2a}$;

$R^{2a}$ is independently, at each occurrence, hydrogen, halogen, $C_{1-6}$ alkyl, $C_{1-6}$ alkoxy, $C_{3-6}$ cycloalkyl, halo $C_{1-6}$ alkyl, hydroxy $C_{1-6}$ alkyl, $C_{5-8}$ aryl or a 5-7 membered heterocyclyl having carbon atoms and 1-4 heteroatoms independently selected from N, O, and S, said aryl or heterocyclyl substituted with 0-2 $R^a$;

$R^a$ is hydrogen, halogen or $C_{1-4}$ alkyl;

or a pharmaceutically-acceptable salt thereof.

5. The compound according to claim 4 wherein:

$R^1$ is $CD_3$ or $C_{1-3}$ alkyl;

$R^2$ is CO—$C_{3-6}$ cycloalkyl, $C_{5-8}$ aryl or a 5-7 heterocyclyl having carbon atoms and 1-4 heteroatoms independently selected from N, O, and S, substituted with 0-4 $R^{2a}$;

$R^{2a}$ is independently, at each occurrence, hydrogen, halogen, $C_{1-6}$ alkyl, $C_{1-6}$ alkoxy, $C_{3-6}$ cycloalkyl, halo $C_{1-6}$ alkyl, hydroxy $C_{1-6}$ alkyl, $C_{5-8}$ aryl or a 5-7 membered heterocyclyl having carbon atoms and 1-4 heteroatoms independently selected from N, O, and S, said aryl or heterocyclyl substituted with 0-2 $R^a$;

$R^a$ is hydrogen, halogen or $C_{1-4}$ alkyl;

or a pharmaceutically-acceptable salt thereof.

6. The compound according to claim 5 wherein:

$R^1$ is $CD_3$;

$R^2$ is CO—$C_{3-6}$ cycloalkyl, $C_{5-8}$ aryl or a 5-7 membered heterocyclyl having carbon atoms and 1-4 heteroatoms independently selected from N, O, and S, substituted with 0-4 $R^{2a}$;

$R^{2a}$ is independently, at each occurrence, hydrogen, halogen, $C_{1-6}$ alkyl, $C_{1-6}$ alkoxy, $C_{3-6}$ cycloalkyl, halo $C_{1-6}$ alkyl, hydroxy $C_{1-6}$ alkyl, $C_{5-8}$ aryl or a 5-7 heterocyclyl having carbon atoms and 1-4 heteroatoms independently selected from N, O, and S, said aryl or heterocyclyl substituted with 0-2 $R^a$;

$R^a$ is hydrogen, halogen or $C_{1-4}$ alkyl;

or a pharmaceutically-acceptable salt thereof.

7. The compound according to claim 1, of the formula

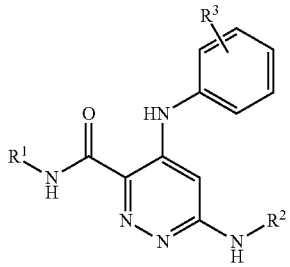

wherein:
- $R^1$ is $CD_3$, $C_{1-3}$ alkyl or $C_{3-6}$ cycloalkyl;
- $R^2$ is CO—$C_{3-6}$ cycloalkyl, $C_{5-8}$ aryl or a 5-7 membered heterocyclyl having carbon atoms and 1-4 heteroatoms independently selected from N, O, and S, substituted with 0-4 $R^{2a}$;
- $R^{2a}$ is independently, at each occurrence, hydrogen, halogen, $C_{1-6}$ alkyl, $C_{1-6}$ alkoxy, $C_{3-6}$ cycloalkyl, halo $C_{1-6}$ alkyl, hydroxy $C_{1-6}$ alkyl, $C_{5-8}$ aryl or a 5-7 membered heterocyclyl having carbon atoms and 1-4 heteroatoms independently selected from N, O, and S, said aryl or heterocyclyl substituted with 0-2 $R^a$;
- $R^a$ is hydrogen, halogen or $C_{1-4}$ alkyl;
- $R^3$ is P(O)—$(C_{1-4}$ alkyl$)_2$;

or a pharmaceutically-acceptable salt thereof.

8. The compound according to claim 1, of the formula

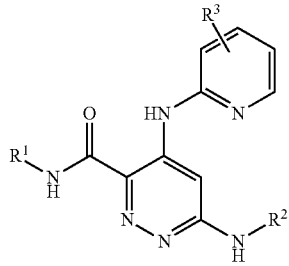

wherein:
- $R^1$ is $CD_3$, $C_{1-3}$ alkyl or $C_{3-6}$ cycloalkyl;
- $R^2$ is CO—$C_{3-6}$ cycloalkyl, $C_{5-8}$ aryl or a 5-7 membered heterocyclyl having carbon atoms and 1-4 heteroatoms independently selected from N, O, and S, substituted with 0-4 $R^{2a}$;
- $R^{2a}$ is independently, at each occurrence, hydrogen, halogen, $C_{1-6}$ alkyl, $C_{1-6}$ alkoxy, $C_{3-6}$ cycloalkyl, halo $C_{1-6}$ alkyl, hydroxy $C_{1-6}$ alkyl, $C_{5-8}$ aryl or a 5-7 heterocyclyl having carbon atoms and 1-4 heteroatoms independently selected from N, O, and S, said aryl or heterocyclyl substituted with 0-2 $R^a$;
- $R^a$ is hydrogen, halogen or $C_{1-4}$ alkyl;
- $R^3$ is P(O)—$(C_{1-4}$ alkyl$)_2$;

or a pharmaceutically-acceptable salt thereof.

9. A pharmaceutical composition comprising one or more compounds according to claim 1 and a pharmaceutically acceptable carrier or diluent.

10. A method of treating a disease, comprising administering to a patient in need of such treatment a therapeutically-effective amount of a compound according to claim 1, wherein the disease is an inflammatory or autoimmune disease selected from multiple sclerosis, rheumatoid arthritis, inflammatory bowel disease, systemic lupus erythematosus, psoriasis, psoriatic arthritis, Crohn's Disease, Siögren's syndrome or scleroderma.

* * * * *

SEQUENCE LISTING

```
<160> NUMBER OF SEQ ID NOS: 1

<210> SEQ ID NO 1
<211> LENGTH: 317
<212> TYPE: PRT
<213> ORGANISM: Homo sapiens

<400> SEQUENCE: 1

Met Gly Ser Ser His His His His His His Ser Ser Gly Glu Thr Val
1               5                   10                  15

Arg Phe Gln Gly His Met Asn Leu Ser Gln Leu Ser Phe His Arg Val
```

-continued

```
                    20                  25                  30
Asp Gln Lys Glu Ile Thr Gln Leu Ser His Leu Gly Gln Gly Thr Arg
            35                  40                  45

Thr Asn Val Tyr Glu Gly Arg Leu Arg Val Glu Gly Ser Gly Asp Pro
    50                  55                  60

Glu Glu Gly Lys Met Asp Glu Asp Pro Leu Val Pro Gly Arg Asp
65                  70                  75                  80

Arg Gly Gln Glu Leu Arg Val Val Leu Lys Val Leu Asp Pro Ser His
                85                  90                  95

His Asp Ile Ala Leu Ala Phe Tyr Glu Thr Ala Ser Leu Met Ser Gln
                100                 105                 110

Val Ser His Thr His Leu Ala Phe Val His Gly Val Cys Val Arg Gly
            115                 120                 125

Pro Glu Asn Ile Met Val Thr Glu Tyr Val Glu His Gly Pro Leu Asp
            130                 135                 140

Val Trp Leu Arg Arg Glu Arg Gly His Val Pro Met Ala Trp Lys Met
145                 150                 155                 160

Val Val Ala Gln Gln Leu Ala Ser Ala Leu Ser Tyr Leu Glu Asn Lys
                165                 170                 175

Asn Leu Val His Gly Asn Val Cys Gly Arg Asn Ile Leu Leu Ala Arg
                180                 185                 190

Leu Gly Leu Ala Glu Gly Thr Ser Pro Phe Ile Lys Leu Ser Asp Pro
        195                 200                 205

Gly Val Gly Leu Gly Ala Leu Ser Arg Glu Glu Arg Val Glu Arg Ile
        210                 215                 220

Pro Trp Leu Ala Pro Glu Cys Leu Pro Gly Gly Ala Asn Ser Leu Ser
225                 230                 235                 240

Thr Ala Met Asp Lys Trp Gly Phe Gly Ala Thr Leu Leu Glu Ile Cys
                245                 250                 255

Phe Asp Gly Glu Ala Pro Leu Gln Ser Arg Ser Pro Ser Glu Lys Glu
                260                 265                 270

His Phe Tyr Gln Arg Gln His Arg Leu Pro Glu Pro Ser Cys Pro Gln
        275                 280                 285

Leu Ala Thr Leu Thr Ser Gln Cys Leu Thr Tyr Glu Pro Thr Gln Arg
    290                 295                 300

Pro Ser Phe Arg Thr Ile Leu Arg Asp Leu Thr Arg Leu
305                 310                 315
```